US012359198B2

(12) United States Patent
Peters et al.

(10) Patent No.: US 12,359,198 B2
(45) Date of Patent: Jul. 15, 2025

(54) HIGH-EFFICACY CRISPRI SYSTEM AND STRONG SYNTHETIC PROMOTERS FOR ALPHAPROTEOBACTERIA AND GAMMAPROTEOBACTERIA

(71) Applicant: Wisconsin Alumni Research Foundation, Madison, WI (US)

(72) Inventors: Jason Peters, Madison, WI (US); Amy Banta, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 25 days.

(21) Appl. No.: 17/501,421

(22) Filed: Oct. 14, 2021

(65) Prior Publication Data

US 2022/0119810 A1    Apr. 21, 2022

Related U.S. Application Data

(60) Provisional application No. 63/092,182, filed on Oct. 15, 2020.

(51) Int. Cl.
*C12N 15/11* (2006.01)
*C12N 9/22* (2006.01)
*C12N 15/63* (2006.01)

(52) U.S. Cl.
CPC .............. *C12N 15/111* (2013.01); *C12N 9/22* (2013.01); *C12N 15/63* (2013.01); *C12N 2310/20* (2017.05); *C12N 2800/10* (2013.01)

(58) Field of Classification Search
CPC .... C12N 15/111; C12N 15/63; C12N 2800/10
See application file for complete search history.

(56) References Cited

U.S. PATENT DOCUMENTS

2021/0071179 A1    3/2021    Peters et al.

FOREIGN PATENT DOCUMENTS

WO    WO-2004003139 A2 *    1/2004    ............. C12N 15/63
WO    WO-2009073551 A2 *    6/2009    ............. C12N 15/72

OTHER PUBLICATIONS

Yang Y et al. Biotechnol Biofuels. Mar. 14, 2019;12:52 (Year: 2019).*
Vigouroux A et al. Microbiol Mol Biol Rev. Apr. 1, 2020;84(2):e00077-19 (Year: 2020).*
Vera JM et al. Jul. 21, 2020;5(4):e00250-20 (Year: 2020).*
Estrem ST et al. Proc Natl Acad Sci U S A. Aug. 18, 1998;95(17):9761-6 (Year: 1998).*
NCBI MK775710.1 (NCBI Database, Jun. 26, 2019) (Year: 2019).*
Peters JM et al. Nat Microbiol. Feb. 2019;4(2):244-250 (Year: 2019).*
Seleem (Seleem M et al. Appl Microbiol Biotechnol. Jan. 2007;73(5):1123-7 (Year: 2007).*
Chain (Chain PS et al. J Bacteriol. Aug. 2011;193(16):4274-5) (Year: 2011).*
Munoz-Gomez (Munoz-Gomez SA et al. Elife. Feb. 25, 2019;8:e42535 (Year: 2019).*
Zheng, Y. et al.; "Characterization and repurposing of the endogenous Type I-F CRISPR-Cas system of Zymomonas mobilis for genome engineering"; Nucleic Acids Research, vol. 47; 2019; pp. 11461-11475.
Baba, T. et al.; "Construction of *Escherichia coli* K-12 in-frame, single-gene knockout mutants: the Keio collection"; Molecular Systems Biology, vol. 2; 2006; 11 pages; DOI: 10.1038/msb4100050.
Banta, A. et al.; "A High-Efficacy CRISPR Interference System for Gene Function Discovery in Zymomonas mobilis"; Applied and Environmental Microbiology, vol. 86, Issue No. 23; 2020; 16 pages; doi: 10.1128/AEM.01621-20.
Belaïch, J-P. et al.; "Influence of Aeration and of Pantothenate on Growth Yields of Zymomonas mobilis"; Journal of Bacteriology. vol. 89, Issue No. 5; 1965; pp. 1195-1200.
Bikard, D. et al.; "Programmable repression and activation of bacterial gene expression using an engineered CRISPR-Cas system"; Nucleic Acids Research, vol. 41, Issue No. 15; 2013; pp. 7429-7437.
Blodgett, J. et al.; "Unusual transformations in the biosynthesis of the antibiotic phosphinothricin tripeptide"; Nature Chemical Biology, vol. 3, Issue No. 8; 2007; pp. 480-485.
Brenac, L. et al.; "Distinct functional roles for hopanoid composition in the chemical tolerance of Zymomonas mobilis"; Molecular Microbiology, vol. 112, Issue No. 5; 2019; pp. 1564-1575.
Choi, Y. et al.; "Metabolic engineering of microorganisms for the production of higher alcohols"; mBio, vol. 5, Issue No. 5; 2014; 10 pages; doi: 10.1128/mBio.01524-01514.
Conway, T.; "The Entner-Doudoroff pathway: history, physiology and 432 molecular biology"; FEMS Microbiology Reviews, vol. 9, Issue No. 1; 1992; pp. 1-27; doi: 10.1111/j.1574-6968.1992.tb05822.x.
Dawes, E. et al.; "The route of ethanol formation in Zymomonas mobilis"; The Biochemical Journal, vol. 98, Issue No. 3; 1966; pp. 795-803.

(Continued)

*Primary Examiner* — Kimberly Chong
*Assistant Examiner* — Douglas Charles Ryan
(74) *Attorney, Agent, or Firm* — Karen A. LeCuyer; DeWitt LLP

(57) ABSTRACT

Described herein are synthetic inducible promoters including 5'-(UP element)-(−35 element)-(spacer element)-(−10 element)-(discriminator element)-3'. Also included are vectors, α-Proteobacteria strains and γ-Proteobacteria strains including the synthetic inducible promoters. A Mobile-CRISPRi plasmid and methods of partially or fully knocking-down expression of a gene in α-Proteobacteria or γ-Proteobacteria are also described. Further included are methods of making an α-Proteobacteria or γ-Proteobacteria strain.

17 Claims, 6 Drawing Sheets

Specification includes a Sequence Listing.

(56) References Cited

OTHER PUBLICATIONS

Estrem S. et al.; "Identification of an UP element consensus sequence for bacterial promoters"; PNAS USA, vol. 95, Issue No. 17; 1998; pp. 9761-9766.

Felczak, M. et al.; "Expression of Phosphofructokinase Is Not Sufficient to Enable Embden-Meyerhof-Parnas Glycolysis in Zymomonas mobilis ZM4"; Frontiers in Microbiology, vol. 10, Article 2270; 2019; 11 pages; doi: 10.3389/fmicb.2019.02270.

Ghosh, I. et al.; "OptSSeq explores enzyme expression and function landscapes to maximize isobutanol production rate"; Metabolic Engineering, vol. 52; 2019; pp. 324-340.

Hawkins, J. et al.; "Modulated efficacy CRISPRi reveals evolutionary conservation of essential gene expression-fitness relationships in bacteria"; Cell Systems; 2019; 15 pages; DOI: 10.1016/j.cels.2020.09.009.

Hawley, D. et al.; "Compilation and analysis of *Escherichia coli* promoter DNA sequences"; Nucleic Acids Research, vol. 11, Issue No. 8; 1983; pp. 2237-2255.

He, M. et al.; "Zymomonas mobilis: a novel platform for future biorefineries"; Biotechnology for Biofuels, vol. 7, Article No. 101; 2014; 15 pages; DOI: https://doi.org/10.1186/1754-6834-7-101.

Hermans, M. et al.; "Content and composition of hopanoids in Zymomonas mobilis under various growth conditions"; Journal of Bacteriology, vol. 173, Issue No. 17; 1991; pp. 5592-5595.

Horbach, S. et al.; "Effect of azasqualene on hopanoid biosynthesis and ethanol tolerance of Zymomonas mobilis"; FEMS Microbiology Letters, vol. 79, Issue No. 2-3; 1991; pp. 347-350.

Jacobson, T. et al.; "2H and 13C metabolic flux analysis elucidates in vivo thermodynamics of the ED pathway in Zymomonas mobilis"; Metabolic Engineering, vol. 54; 2019; pp. 301-316; doi: 10.1016/j.ymben.2019.05.006.

Jost, M. et al.; "Titrating gene expression using libraries of systematically attenuated CRISPR guide RNAs"; Nature Biotechnology, vol. 38, Issue No. 3; 2020; pp. 355-364.

Kalnenieks, U. et al.; "Modeling of Zymomonas mobilis central metabolism for novel metabolic engineering strategies"; Frontiers in Microbiology, vol. 42; 2014; 7 pages; doi: 10.3389/fmicb.2014.00042.

Khan, S. et al.; "Broad-Host-Range Expression Vectors with Tightly Regulated Promoters and Their Use to Examine the Influence of TraR and TraM Expression on Ti Plasmid Quorum Sensing"; Applied and Environmental Microbiology, vol. 74, Issue No. 16; 2008; pp. 5053-5062.

Kulkarni, G. et al.; "Specific hopanoid classes differentially affect free-living and symbiotic states of Bradyrhizobium diazoefficiens"; mBio, vol. 6, Issue No. 5; 2015; 9 pages; doi: 10.1128/mBio.01251-01215.

Lal, P. et al.; "Improving Mobilization of Foreign DNA into Zymomonas mobilis Strain ZM4 by Removal of Multiple Restriction Systems"; Applied and Environmental Microbiology, vol. 87, Issue No. 19; 2021; 16 pages; doi: 10.1128/AEM.00808-21.

Lee, K. et al.; "The genome-scale metabolic network analysis of Zymomonas mobilis ZM4 explains physiological features and suggests ethanol and succinic acid production strategies"; Microbial Cell Factories, vol. 9, Article No. 94; 2010; 12 pages.

Liu, X. et al.; "High-throughput CRISPRi phenotyping identifies new essential genes in *Streptococcus pneumoniae*"; Molecular Systems Biology, vol. 13, Issue No. 5; 2017; 18 pages; doi: 10.15252/msb.20167449.

Müh, U. et al.; "A Xylose-Inducible Expression System and a CRISPR Interference Plasmid for Targeted Knockdown of Gene Expression in Clostridioides difficile"; Journal of Bacteriology, vol. 201, Issue No. 14; 2019; 12 pages; DOI: https://doi.org/10.1128/JB.00711-18.

Nouri, H. et al.; "A reconciliation of genome-scale metabolic network model of Zymomonas mobilis ZM4"; Scientific Reports, vol. 10, Article No. 7782; 2020; 11 pages.

Pédelacq, J-D. et al.; "Engineering and characterization of a superfolder green fluorescent protein"; Nature Biotechnology, vol. 24, Issue No. 1; 2006; pp. 79-88.

Peters, J. et al.; "A Comprehensive, CRISPR-based Functional Analysis of Essential Genes in Bacteria"; Cell, vol. 165; 2016; pp. 1493-1506.

Peters, J. et al.; "Enabling genetic analysis of diverse bacteria with Mobile-CRISPRi"; Nature Microbioogy, vol. 4; 2019; pp. 244-250.

Qi, L. et al.; "Repurposing CRISPR as an RNA-guided platform for sequence-specific control of gene expression"; Cell, vol. 152; 2013; pp. 1173-1183.

Qiu, M. et al.; "Metabolic engineering of Zymomonas mobilis for anaerobic isobutanol production"; Biotechnology for Biofuels, vol. 13, Article No. 15; 2020; 14 pages; DOI: https://doi.org/10.1186/s13068-020-1654-x.

Qu, J. et al.; "Modulating pathogenesis with Mobile-CRISPRi"; Journal of Bacteriology, vol. 201, Issue No. 22; 2019; 9 pages; DOI: 10.1128/JB.00304-19.

Rath, D. et al.; "Efficient programmable gene silencing by Cascade"; Nucleic Acids Research, vol. 43; 2015; pp. 237-246.

Roberts, R. et al.; "REBASE—a database for DNA restriction and modification: enzymes, genes and genomes"; Nucleic Acids Research, vol. 43; 2015; pp. D298-D299.

Rousset, F. et al.; "Genome-wide CRISPR-dCas9 screens in *E. coli* identify essential genes and phage host factors"; PLOS Genetics, vol. 14, Issue No. 11; 2018; 18 pages; DOI: https://doi.org/10.1371/journal.pgen.1007749.

Sadler, J. et al.; "A perfectly symmetric lac operator binds the lac repressor very tightly"; PNAS USA, vol. 80, Issue No. 22; 1983; pp. 6785-6789.

Sáenz, J. et al.; "Hopanoids as functional analogues of cholesterol in bacterial membranes"; PNAS USA, vol. 112, Issue No. 38; 2015; pp. 11971-11976.

Schmerk, C. et al.; "Hopanoid production is required for low-pH tolerance, antimicrobial resistance, and motility in Burkholderia cenocepacia"; Journal of Bacteriology, vol. 193, Issue No. 23; 2011; pp. 6712-6723.

Silipo, A. et al.; "Covalently linked hopanoid-lipid A improves outer-membrane resistance of a Bradyrhizobium symbiont of legumes"; Nature Communications, vol. 5; 2014; 11 pages; doi: 10.1038/ncomms6106.

Skerker, J. et al.; "Dissecting a complex chemical stress: chemogenomic profiling of plant hydrolysates"; Molecular Systems Biology, vol. 9, Issue No. 674; 2013; 21 pages; doi: 10.1038/msb.2013.30.

Vigoroux, A. et al.; "CRISPR Tools to Control Gene Expression in Bacteria"; Microbiology and Molecular Biology Reviews, vol. 84, Issue No. 2; 2020; 18 pages; doi: 10.1128/MMBR.00077-19.

Wang, T. et al.; "Pooled CRISPR interference screening enables genome-scale functional genomics study in bacteria with superior performance"; Nature Communications, vol. 9, Article No. 2475; 2018; 15 pages; doi: https://doi.org/10.1038/s41467-018-04899-x.

Wecker, M. et al.; "Production of Acetaldehyde by Zymomonas mobilis"; Applied Environmental Microbiology, vol. 53, Issue No. 12; 1987; pp. 2815-2820.

Welander, P. et al.; "Hopanoids play a role in membrane integrity and pH homeostasis in Rhodopseudomonas palustris TIE-1"; Journal of Bacteriology, vol. 191, Issue No. 19; 2009; pp. 6145-6156.

Wu, B. et al.; "Engineered Zymomonas mobilis tolerant to acetic acid and low pH via multiplex atmospheric and room temperature plasma mutagenesis"; Biotechnology for Biofuels, vol. 12, Article No. 10; 2019; 13 pages; DOI: https://doi.org/10.1186/s13068-018-1348-9.

Wu, C-H. et al.; "Methylation 453 at the C-2 position of hopanoids increases rigidity in native bacterial membranes"; eLife, vol. 4, e05663; 2015; doi: 10.7554/eLife.05663.

Yang, S. et al.; "Complete genome sequence and the expression pattern of plasmids of the model ethanologen Zymomonas mobilis ZM4 and its xylose-utilizing derivatives 8b and 2032"; Biotechnol biofuels, vol. 11; Article 125; 2018; 20 pages; DOI: 10.1186/s13068-018-1116-x.

Yang, S. et al.; "Zymomonas mobilis as a model system for production of biofuels and biochemicals"; Microbial Biotechnology, vol. 9, Issue No. 6; 2016; pp. 699-717.

Yang, Y. et al.; "Prediction and characterization of promoters and ribosomal binding sites of Zymomonas mobilis in system biology

(56) References Cited

OTHER PUBLICATIONS era"; Biotechnology for Biofuels, vol. 12, Article No. 52; 2019; DOI: https://doi.org/10.1186/s13068-019-1399-6.

Hawkins et al., "Mismatch-CRISPRi reveals the co-varying expression-fitness relationships of essential genes in *Echerichia coli* and *Bacillus subtilis*", Cell Syst., vol. 11, No. 5, Nov. 18, 2020; pp. 523-535.

Jost, Marco et al. Titrating gene expression using libraries of systematically attenuated CRISPR guide RNAs, Nat Biotechnol. Mar. 2020 ; 38(3): 355-364.

Vigouroux, Antoine, et al. Tuning dCas9's ability to block transcription enables robust, noiseless knockdown of bacterial genes, Mol Syst Biol. (2018) 14: e7899, 1-14.

Hall et al., "Tools for Genetic Engineering and Gene Expression Control in *Novosphingobium aromaticivorans* and *Rhodobactersphaeroides*", bioRxiv [Preprint]. Aug. 26, 2023:2023. 08.25.554875; doi: 10.1101/2023.08.25.554875.

\* cited by examiner

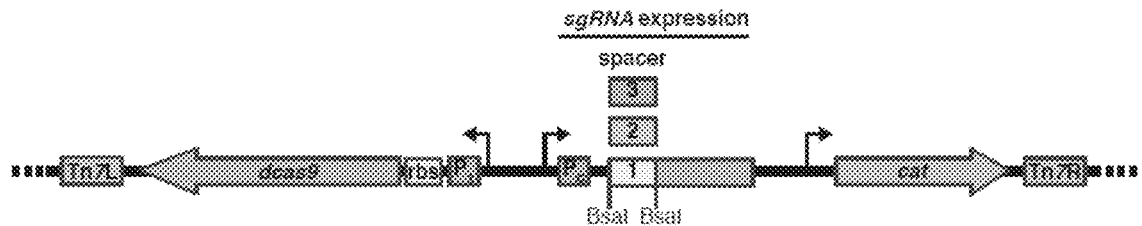

FIG. 1

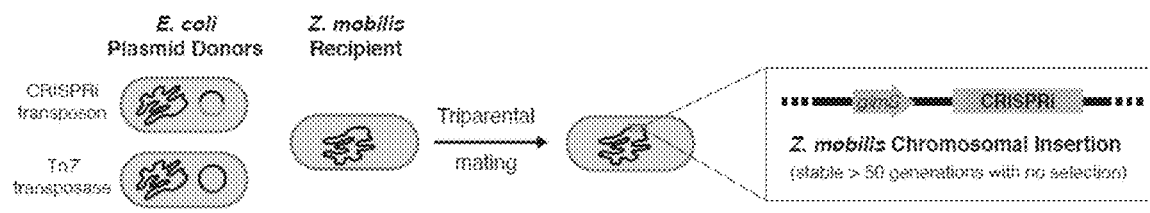

FIG. 2

| | Promoter sequence | SEQ ID NO: |
|---|---|---|
| A | CTCACTCATTAGGCACCCCAGGCTTTACACTTTATGCTTCCGGCTCGTATAATGTCTAGT | 1 |
| B | CTCACTCATTAGGCACCCCAGGCTTTACAATTGTGAGCGGCTCACAATATAATGTCTAGT | 2 |
| C | GGAAAATTTTTTTCAAAAGTACTTGAAAATTGTGAGC•GCTCACAATATAATTCTAGT | 3 |
| D | GGAAAATTTTTTTCAAAAGTACTTGAATTGTGAGCG•GATAACAATATAATTCTAGT | 4 |
| E | GGAAAATTTTTTTCAAAAGTACTTTACAATTGTGAGCGCTCACAATATAATTCTAGT | 5 |
| F | GGAAAATTTTTTTCAAAAGTACTTTAAATTGTGAGCGGATAACAATATAATTCTAGT | 6 |
| | nnnnnnnnnnnnnnnnnnnnnnnnTTGACAnnnnnnnnn•nnnnnnnnnTATAATnnnnnn | 7 |
| |                              -35        spacer      -10 | |

FIG. 3

HIGH-EFFICACY CRISPRI SYSTEM AND STRONG SYNTHETIC PROMOTERS FOR ALPHAPROTEOBACTERIA AND GAMMAPROTEOBACTERIA

CROSS-REFERENCE OF RELATED APPLICATIONS

This application claims benefit of U.S. Provisional Patent Application No. 63/092,182, filed on Oct. 15, 2020, which is incorporated by reference herein in its entirety.

STATEMENT REGARDING FEDERALLY SPONSORED RESEARCH & DEVELOPMENT

This invention was made with government support under DE-SC0018409 awarded by the US Department of Energy. The government has certain rights in the invention.

SEQUENCE LISTING

The Instant Application contains a Sequence Listing which has been submitted electronically in XML format and is hereby incorporated by reference in its entirety. Said XML copy, created on Oct. 6, 2021 is named 8TZ6708.PDF and is 13.4 KB (13,728 bytes) in size. The Sequence Listing does not go beyond the disclosure in the application as filed.

FIELD OF THE DISCLOSURE

The present disclosure is related to novel synthetic promotors and gene knockdown methods, particularly in α-Proteobacteria such as *Zymomonas mobilis* as well as γ-Proteobacteria.

BACKGROUND

Biofuels are renewable and sustainable energy sources that promise to mitigate climate change and improve energy security. *Zymomonas mobilis* is a Gram-negative alphaproteobacterium with superlative properties for biofuel production but poorly characterized gene functions. *Z. mobilis* is a promising biofuel producer due to its high alcohol tolerance (resistant to ethanol up to 16% vol/vol) and streamlined metabolism that efficiently converts sugar to ethanol. Engineered strains of *Z. mobilis* can convert sugars extracted from plant feed stocks into next generation biofuels such as isobutanol. *Z. mobilis* genes are poorly characterized relative to model bacteria, hampering the ability to rationally engineer the genome with pathways capable of converting sugars from plant hydrolysates into valuable biofuels and bioproducts. Many of the unique properties that make *Z. mobilis* an attractive biofuel producer are controlled by essential genes: however, these genes cannot be manipulated using traditional genetic approaches (e.g., deletion or transposon insertion) because they are required for viability.

What is needed are compositions and methods for editing of essential genes in α-Proteobacteria such as *Z. mobilis* and other bacteria.

BRIEF SUMMARY

In an aspect, a synthetic inducible promoter comprises 5'-(UP)-(−35 element)-(spacer element)-(−10 element)-(discriminator element)-3'; wherein
the (UP element) is $N_1N_2AAN_3N_4N_5N_6N_7TTN_8N_9N_{10}N_{11}N_{12}N_{13}N_{14}AN_{15}N_{16}N_{17}N_{18}$ (SEQ ID NO: 8), wherein $N_1$, $N_2$, $N_8$, $N_{10}$, $N_{11}$, $N_{12}$, and $N_{18}$ are each independently A, T, G or C; $N_3$ is T, A or C; $N_4$, $N_5$, $N_6$, $N_7$, $N_{13}$, and $N_{14}$ are each independently T or A; No is T or C; $N_{15}$ is C or G; $N_{16}$ is C, G or T; and $N_{17}$ is C, A or G; or
GAAAATTTTTTTTAAAAAAAAAN$_{18}$ (SEQ ID NO: 9), wherein $N_{18}$ is A, T, G or C; or
TTGCTGCTCGTAAAAAAAAAAN$_{19}$ (SEQ ID NO: 10), wherein $n_{19}$ is A, T, G or C;
the (−35 element) is $TTN_{20}N_{21}N_{22}A$, wherein $N_{20}$ is A, C or T; $N_{21}$ is G or T; $N_{22}$ is A, C, G or T;
the (spacer element) is ATTGTGAGCGCTCACAAT (SEQ ID NO: 11), TTGTGAGCGCTCACAAT (SEQ ID NO: 12), or TGTGAGCGGATAACAAT (SEQ ID NO: 13),
the (−10 element) is $TAN_{23}N_{24}N_{25}N_{26}$, wherein $N_{23}$, $N_{24}$, $N_{25}$, and $N_{26}$ are A, C, G or T; and
the (discriminator element) is $N_{27}N_{28}N_{29}N_{30}N_{31}N_{32}$, wherein $N_{27}$, $N_{28}$, $N_{29}$, $N_{30}$, $N_{31}$ and $N_{32}$ are each independently A, C, G or T.

Also included are vectors comprising the above-described synthetic promoter.

In another aspect, an α-Proteobacteria or γ-Proteobacteria strain comprises the inducible promoter described above.

In yet another aspect, a Mobile-CRISPRi plasmid comprises, in operable communication,
an expression cassette for a dCas9 protein, the dCas9 protein expressed with a strong α-Proteobacteria or γ-Proteobacteria ribosome binding site; and
a gRNA expression cassette under control of the synthetic inducible promoter described above,
wherein a gRNA-dCas9 complex produced from the Mobile CRISPRi plasmid partially or fully blocks expression of an α-Proteobacteria or γ-Proteobacteria gene.

In a further aspect, a population of Mobile CRISPRi plasmids is included, wherein each individual species of the population comprises a gRNA library member comprising a unique gRNA spacer sequence.

In another aspect, method of partially or fully knocking-down expression of a gene in α-Proteobacteria or γ-Proteobacteria comprises transferring the Mobile-CRISPRi plasmid described above into the α-Proteobacterium or γ-Proteobacterium and expressing the dCas9 protein and the gRNA.

In yet another aspect, a method of making an α-Proteobacteria or γ-Proteobacteria strain comprising a chromosomally inserted Mobile-CRISPRi expression cassette comprises
triparental mating a first *E. coli* donor strain and a second *E. coli* donor strain and an α-Proteobacteria or γ-Proteobacteria recipient,
wherein the first *E. coli* donor strain comprises a plasmid encoding a Tn7 transposase,
wherein the second *E. coli* donor strain comprises a Tn7 transposon encoding the Mobile CRISPRi expression cassette, and
wherein the Mobile-CRISPRi expression cassette comprises an expression cassette for a dCas9 protein, the dCas9 protein expressed with a strong α-Proteobacteria or γ-Proteobacteria ribosome binding site; and a gRNA expression cassette under control of the synthetic inducible promoter described above, wherein a gRNA-dCas9 complex produced from the Mobile CRISPRi plasmid partially or fully blocks expression of an α-Proteobacteria or γ-Proteobacteria gene; and producing the α-Proteobacteria or γ-Proteobacteria strain comprising the chromosomally inserted Mobile-CRISPRi expression cassette.

BRIEF DESCRIPTION OF THE DRAWINGS

FIG. 1 is a schematic of a Mobile-CRISPRi system for transcriptional repression optimized for Z. mobilis. A modular Z. mobilis CRISPRi system encodes dCas9, sgRNA, and antibiotic resistance cassettes on a Tn7 transposon. The promoter (P1) and ribosome binding site (rbs) for dCas9 as well as the promoter (Pc) for the sgRNA have been optimized for Z. mobilis. DNA encoding the 20 nt variable region of the sgRNA can be cloned (individually or libraries) in between the BsaI sites.

FIG. 2 illustrates the CRISPRi expressing strains constructed by triparental mating of E. coli donor strains-one harboring the Mobile-CRISPRi plasmid and another harboring a plasmid expressing the Tn7 transposase with Z. mobilis. The CRISPRi expression cassette will be stably incorporated onto the Z. mobilis chromosome at the Tn7 att site located downstream of glmS.

FIG. 3 shows the optimization of sgRNA expression. Six promoter sequences (A-F) based on either lacUV5 or a synthetic promoter were incorporated into the CRISPRi system. The −10 and −35 core promoter elements are underlined and shown in bold, lac operator locations are highlighted (O1) or (symmetric operator), as well as the UP element.

Figure 4:
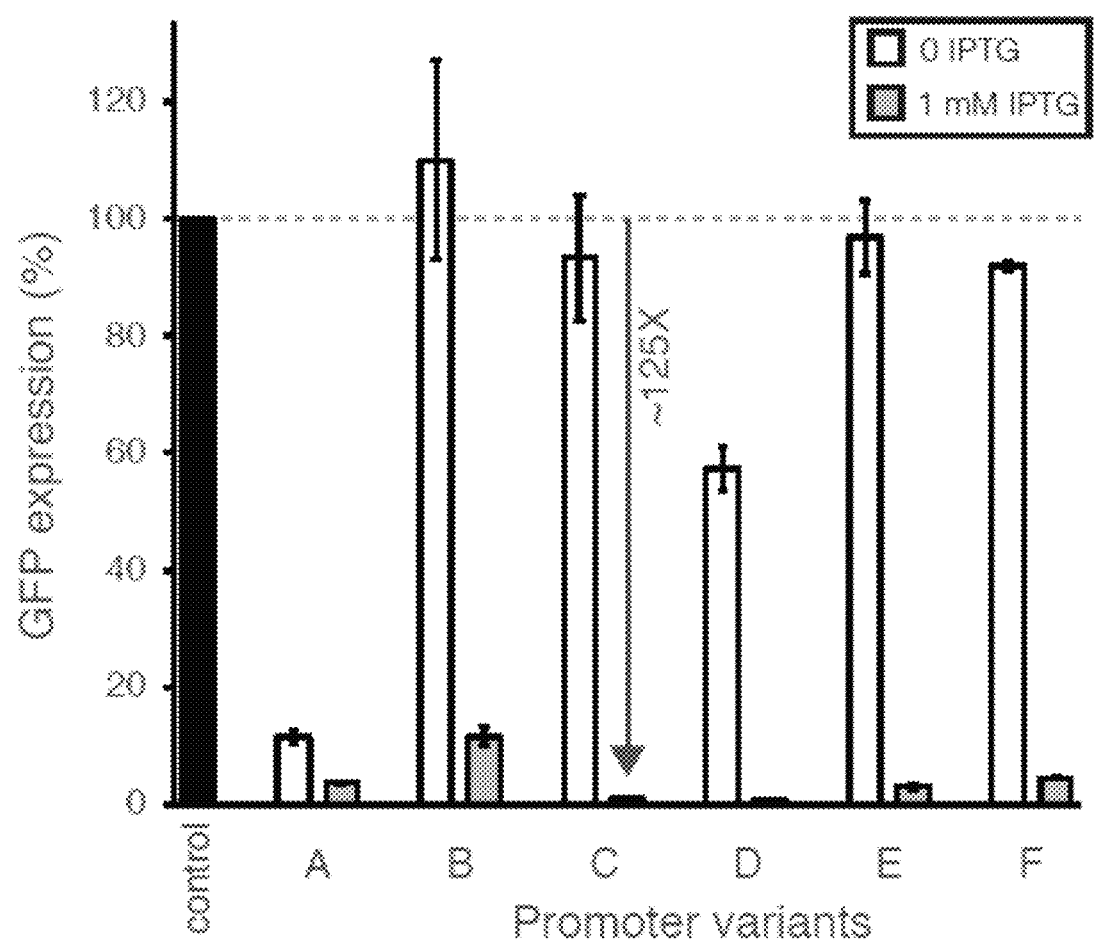
FIG. 4 shows a comparison of Z. mobilis Mobile-CRISPRi sgRNA promoter variants. A GFP expression cassette was cloned into the PmeI site and a sgRNA targeting GFP (or a non-targeting control) was cloned into the BsaI sites. Cultures were diluted 1:1000 and incubated in medium with 0 or 1 mM IPTG for ~10 doublings prior to measurement of GFP expression. Expression was normalized to a non GFP-expressing strain. Standard deviation between 4 biological replicates is shown.

The above-described and other features will be appreciated and understood by those skilled in the art from the following detailed description, drawings, and appended claims.

DETAILED DESCRIPTION

Described herein are novel synthetic promoters, and vectors comprising the synthetic promoters. The synthetic promoters and vectors are useful for expression of single guide RNA (sgRNA), for example, in α-Proteobacteria such as rhodobacter species, Zymomonas mobilis and Novosphingobium aromaticivorans, and γ-Proteobacteria including pathogens such as Acinetobacter baumannii.

Specifically, established herein is a stable, high-efficacy CRISPRi system in Z. mobilis that is capable of perturbing all genes-including essential genes. Z. mobilis CRISPRi causes either strong knockdowns (>100-fold) using single guide RNA (sgRNA) spacers that perfectly match target genes, or partial knockdowns using spacers with mismatches. The efficacy of Z. mobilis CRISPRi was established by targeting essential genes that are universally conserved in bacteria, key to the efficient metabolism of Z. mobilis, or underlie alcohol tolerance. The Z. mobilis CRISPRi system described herein enables comprehensive gene function discovery, opening a path to rational design of biofuel production strains with improved yields.

Z. mobilis is a Gram-negative α-Proteobacterium with superlative properties for biofuel production. The ability to engineer strains of Z. mobilis that produce high yields of advanced biofuels, such as isobutanol (IBA), using sugars from lignocellulosic hydrolysates has been stymied by the lack of functional information for two key gene sets: metabolic and stress response/resistance genes. Genetic analysis to identify and characterize metabolic and stress response genes will enable engineering of strains with increased flux toward IBA and away from ethanol, as well as strains that are resistant to hydrolysate inhibitors such as acetic acid and various phenolic compounds.

Z. mobilis has a minimalistic metabolism with little functional redundancy. Z. mobilis converts sugars to pyruvate via the Entner-Doudoroff (ED) pathway, rather than the more commonly used but less thermodynamically favorable Embden-Meyerhof-Parnas pathway (EMP). Metabolic models based on Z. mobilis ZM4 genome sequences revealed that central metabolic pathways such as glycolysis and the tricarboxylic acid (TCA) cycle are missing key enzymes (e.g., 6-phosphofructokinase and 2-oxoglutarate dehydrogenase, respectively), further limiting its metabolic plasticity. Because of its streamlined metabolism, many metabolic genes are predicted to be essential for growth in Z. mobilis.

Another defining feature of Z. mobilis physiology is the production of large quantities of hopanoids, i.e., triterpenoid lipids that provide resistance to environmental stresses in bacteria. Hopanoids are thought to act by altering membrane fluidity analogous to the action of cholesterol—also a triterpenoid lipid—on eukaryotic membranes. Although other bacteria make hopanoids, Z. mobilis produces them in much higher quantities, with the number of hopanoids nearly matching that of phospholipids in the cell during peak production conditions. Hopanoids are thought to be essential to Z. mobilis, as chemical inhibition of enzymes involved in hopanoid precursor biosynthesis inhibits growth and transposon insertions into hopanoid biosynthesis genes result in cells with both a wild-type and transposon mutant allele (i.e., hpn+/hpn::Tn strains). Consistent with having an essential role in *Z. mobilis* physiology, hopanoid production is correlated with ethanol content of the growth medium, and mutations in hopanoid biosynthesis genes increase sensitivity to ethanol. Whether hopanoids are required for resistance to additional stresses, such as hydrolysate toxins or alcohols other than ethanol is unknown.

CRISPR interference (CRISPRi) is a programmable gene knockdown system that can precisely control the timing and extent of gene repression. Because CRISPRi knockdowns are inducible and titratable, the steps of strain construction and gene phenotyping are separable, enabling targeting of essential genes. CRISPRi has been used to phenotype essential genes in multiple bacterial species, defining chemical-gene interactions, cell morphology phenotypes, host genes involved in phage life cycles, novel gene functions, and essential gene network architecture, among others.

Previously, "Mobile-CRISPRi", a suite of modular CRISPRi vectors based on the extensively studied type II-A CRISPR system from *Streptococcus pyogenes* (i.e., Spy dCas9; FIG. 1) that are transferred by mating and site-specifically integrate into the genomes of recipient bacteria, was developed. Integration and knockdown in species ranging from Gram-negative γ-Proteobacteria to Gram-positive Firmicutes was demonstrated. Notably, species from α-Proteobacteria were not tested. *Z. mobilis* contains a native type I-F CRISPR system that has been co-opted for efficient genome editing as well as CRISPRi in a Cas3 nuclease-deficient background; however, CRISPRi using the native system showed low knockdown efficacy (4-5 fold maximum) and was not inducible as constructed, limiting its usefulness in targeting essential genes. As shown herein, importing the heterologous Spy dCas9 system results in stronger knockdowns, as is seen in other species.

The synthetic promoters and vectors described herein can be used in a high-efficacy CRISPRi system in *Z. mobilis* that is capable of perturbing all genes—including essential genes. A stable and efficacious CRISPRi system for *Z. mobilis* based on Spy dCas9 has been developed. A strong (>100-fold) or partial knockdown of gene expression was demonstrated by using sgRNA spacers that are complementary or mismatched to target genes, respectively. *Z. mobilis* CRISPRi can clarify the essentiality of genes involved in metabolism and hopanoid biosynthesis. Further, reduced expression of specific hopanoid biosynthesis genes leads to IBA sensitivity. The *Z. mobilis* CRISPRi system described herein enables rapid characterization of gene function, speeding the way to rational engineering of the genome for advanced biofuel production.

As a first step to developing a CRISPRi system for *Z. mobilis* as well as other α-Proteobacteria, novel synthetic promoters were developed. While the novel synthetic promoters are useful for guide RNA (gRNA, e.g., sgRNA) and dCas9 protein expression as described herein, they are not limited to such uses. LacI-regulated synthetic promoters based on *Escherichia coli* σ$^{70}$ consensus elements were developed to increase sgRNA expression to a higher level than lacUV5.

Bacterial promoters typically include three RNA polymerase (RNAP)-specific motifs: the UP element, the −10 element and the −35 element. The UP element is an AT-rich region located upstream of the −35 element that is recognized by the RNAP α-subunit. The −10 and −35 elements are recognized by the σ subunit of RNAP. The spacer element between the −35 and −10 element binds the lactose repressor of *Escherichia coli*, for example. The discriminator element is found between the −10 element and the transcription start site and interacts with the σ$_{1,2}$ RNAP subunit.

In an aspect, a synthetic inducible promoter comprises 5'-(UP element)-(−35 element)-(spacer element)-(−10 element)-(discriminator element)-3'; wherein
the (UP element) is $N_1N_2AAN_3N_4N_5N_6N_7TTN_8N_9N_{10}N_{11}N_{12}N_{13}N_{14}AN_{15}N_{16}N_{17}N_{18}$ (SEQ ID NO: 8), wherein $N_1$, $N_2$, $N_8$, $N_{10}$, $N_{11}$, $N_{12}$, and $N_{18}$ are each independently A, T, G or C; $N_3$ is T, A or C; $N_4$, $N_5$, $N_6$, $N_7$, $N_{13}$, and $N_{14}$ are each independently T or A; $N_9$ is T or C; $N_{15}$ is C or G; $N_{16}$ is C, G or T; and $N_{17}$ is C, A or G; or
$GAAAATTTTTTTTAAAAAAAAAN_{18}$ (SEQ ID NO: 9), wherein $N_{18}$ is A, T, G or C; or
$TTGCTGCTCGTAAAAAAAAAAN_{19}$ (SEQ ID NO: 10), wherein —$N_{19}$ is A, T, G or C;
the (−35 element) is $TTN_{20}N_{21}N_{22}A$, wherein $N_{20}$ is A, C or T; $N_{21}$ is G or T; $N_{22}$ is A, C, G or T;
the spacer element is ATTGTGAGCGCTCACAAT (SEQ ID NO: 11), TTGTGAGCGCTCACAAT (SEQ ID NO: 12), or TGTGAGCGGATAACAAT (SEQ ID NO: 13),
the (−10 element) is $TAN_{23}N_{24}N_{25}N_{26}$, wherein $N_{23}$, $N_{24}$, $N_{25}$, and $N_{26}$ are A, C, G or T; and
the discriminator element is $N_{27}N_{28}N_{29}N_{30}N_{31}N_{32}$, wherein $N_{27}$, $N_{28}$, $N_{29}$, $N_{30}$, $N_{31}$ and $N_{32}$ are each independently A, C, G or T.

Exemplary "UP" elements include:

```
                              (SEQ ID NO: 14)
GGAAAATTTTTTTCAAAAGTAC, (SEQ ID NO: 15)
GGAAAATTTTTTTCAAAAGTAN₁₈, (SEQ ID NO: 16)
AGAAATTTTTTTCGAAAAACAN₁₈, (SEQ ID NO: 17)
TAAAAATTTTTTTGAAAAGGGN₁₈, (SEQ ID NO: 18)
CAAAAATATTTTTGAAAAAAGAN₁₈, (SEQ ID NO: 19)
GGAAATATTTTTTCATAAACCCN₁₈, (SEQ ID NO: 20)
AGAAAAATATTTTCGAAAACTAN₁₈, (SEQ ID NO: 21)
AAAAATATTTTTCGAAAAGTAN₁₈, (SEQ ID NO: 22)
TAAATTTTTTTTGCAAAAGTAN₁₈, (SEQ ID NO: 23)
ACAAAAATATTTTTCAAAACCCN₁₈, (SEQ ID NO: 24)
TTAAATTTTTTTCGTAAACCCN₁₈, (SEQ ID NO: 25)
TTAAATTTTTTTTCATAAACCCN₁₈, (SEQ ID NO: 26)
TCAAATTTTTTTTGCAAACCCN₁₈, (SEQ ID NO: 27)
CAAATTTTTTTTGCTAAACCCN₁₈,
```

-continued

AAAAATATTTTTTGAAAAGTAN₁₈, (SEQ ID NO: 28)

TAAAAATATTTTTCGTTTACCCN₁₈, (SEQ ID NO: 29)

ACAAAAATATTTTTCGAAACCCN₁₈, (SEQ ID NO: 30)

TCAAAATTTTTTTGCAAAGTAN₁₈, (SEQ ID NO: 31)

TGAATTTTTTTTCGTCTACCCN₁₈, (SEQ ID NO: 32)

AGAAAAATATTTTTGAAAACTAN₁₈, (SEQ ID NO: 33)

GCAAAATAATTGTAAAAAAGTAN₁₈, (SEQ ID NO: 34)

AGAAATTTATTTTAAAAAAGGGN₁₈, (SEQ ID NO: 35)

TGAAAAATATTTTTGAAAACTAN₁₈, (SEQ ID NO: 36)

TAAACTATTTTTCAAAAAGGAN₁₈, (SEQ ID NO: 37)

TGAAATATTTTTTGCGAAAGGGN₁₈, (SEQ ID NO: 38)

TAAACTTTTTTTTCGAAAGTGN₁₈, (SEQ ID NO: 39)

TGAAATATTTTTTGAAAACCCN₁₈, (SEQ ID NO: 40)

AGATTTTTTTTTGTAAAAGTGN₁₈, (SEQ ID NO: 41)

GCAAAAATATTTCGTCAAACCCN₁₈, (SEQ ID NO: 42)

GAAAAATATTTTTGATAAAGTAN₁₈, (SEQ ID NO: 43)

GCAAAATTATTTTGCTAAAGTAN₁₈, (SEQ ID NO: 44)

GAAAATATATTTTTCAAAAGTAN₁₈, (SEQ ID NO: 45)

CTCACTCATTAGGCACCCCAGGC, (SEQ ID NO: 46)

GAAAATTTTTTTAAAAAAAAAAN₁₈, (SEQ ID NO: 9)
and

TTGCTGCTCGTAAAAAAAAAAN₁₉. (SEQ ID NO: 10)

The UP elements of SEQ ID NOs. 14-36 were identified in SELEX experiments. The UP elements of SEQ ID NOS. 9 and 10 were identified by engineering. Without being held to theory, it is believed that the UP element engages RNAP by binding as well as by the shape of the DNA. It is expected that many of the sequences within the scope of SEQ ID NO: 8 will function as UP elements.

The (−35 element) is $TTN_{20}N_{21}N_{22}A$, wherein $N_{20}$ is A, C or T; $N_{21}$ is G or T; $N_{22}$ is A, C, G or T. The sequence of the −35 element is determined by the lac repressor binding site. The −35 element and the position of the −35 element can be shifted. Exemplary −35 elements include TTKHRA, TTKHAA and TTKHAA, wherein K is A, C or T; H is G or T; and R is A, C, G or T. Specific −35 elements include TTTACA, TTGAAA, TTGAAT, and TTTAAA.

The (spacer element) is ATTGTGAGCGCTCACAAT (SEQ ID NO: 11), TTGTGAGCGCTCACAAT (SEQ ID NO: 12), or TGTGAGCGGATAACAAT (SEQ ID NO: 13). The spacer element between the −35 and −10 element binds the lactose repressor of *Escherichia coli*. The symmetric lac operator used in promoters B, C, and E binds LacI more tightly than wild-type operators used in promoters D and F.

The (−10 element) is $TAN_{23}N_{24}N_{25}N_{26}$, Wherein $N_{23}$, $N_{24}$, $N_{25}$, and $N_{26}$ are A, C, G or T. Exemplary −10 sequences include TATAAT. In γ-Proteobacteria, the terminal N must be a T, while in α-Proteobacteria, the terminal N can be any nucleotide.

The (discriminator element) is $N_{27}N_{28}N_{29}N_{30}N_{31}N_{32}$, wherein $N_{27}$, $N_{28}$, $N_{29}$, $N_{30}$, $N_{31}$ and $N_{32}$ are each independently A, C, G or T. Exemplary discriminator elements include GTCTAGT and TCTAGT.

In an aspect, the synthetic inducible promoter is Promoter C (SEQ ID NO: 3), Promoter D (SEQ ID NO: 4), Promoter E (SEQ ID NO: 5) or Promoter F (SEQ ID NO: 6).

In an aspect, the synthetic inducible promoter is inducible with Isopropyl β-d-1-thiogalactopyranoside (IPTG), or lactose.

Also included herein are vectors comprising the synthetic inducible promoters described herein. Exemplary vectors include plasmids known in the art which are suitable for expression in α-Proteobacteria and γ-Proteobacteria such as plasmids that can be propagated in *E. coli*. Exemplary vectors include vectors with pBBR1, pRSF1030, or pIND4 origins. Plasmids include pBBR1 or variations thereof such as pBBR1-MCS1-5, pSRK-kan, pSRK-gent, and pRL814. Additional plasmids suitable for α-Proteobacteria include pIND4.

Also included herein are α-Proteobacteria and γ-Proteobacteria strains comprising the inducible promoters described herein.

Exemplary α-Proteobacteria strains include *Z. mobilis, Novosphingobium aromaticivorans, Rhodobacter sphaeroides*, and *Agrobacterium tumefaciens*.

Exemplary γ-Proteobacteria strains include *Acinetobacter baumannii, Escherichia coli, Enterobacter cloacae, Klesbiella pneumoniae, Klebsiella oxytoca, Klebsiella aerogenes, Pseudomonas aeruginosa, Pseudomonas syringae*, and *Pseudomonas putida*.

Also included herein are Mobile-CRISPRi plasmids which can be used for gene knockdown in α-Proteobacteria and γ-Proteobacteria. A Mobile-CRISPRi plasmid, comprises, in operable communication, an expression cassette for a dCas9 protein, the dCas9 protein expressed with a strong α-Proteobacteria or γ-Proteobacteria ribosome binding site; a gRNA expression cassette under control of a synthetic inducible promoter as described herein; wherein a gRNA-dCas9 complex produced from the Mobile-CRISPRi plasmid partially or fully blocks expression of an α-Proteobacteria or γ-Proteobacteria gene.

Cas9 is a dual RNA-guided DNA endonuclease enzyme associated with the Clustered Regularly Interspaced Short Palindromic Repeats (CRISPR) adaptive immune system in *Streptococcus pyogenes*. dCas9 refers to Cas9 variants without endonuclease activity, which are used in CRISPR systems along with gRNAs to target specific genes or nucleotides complementary to the gRNA with PAM sequences that allow the dCas9 to bind. Although dCas9 lacks endonuclease activity, it is still capable of binding to its guide RNA and the DNA strand that is being targeted. In an aspect, the dCas9 is *Streptococcus pyogenes* dCas9, a *Homo sapiens* codon-optimized *S. pyogenes* dcas9 (See, e.g., WO2014/197748), and other dCas9 variants known in the art.

As used herein, a guide RNA or gRNA includes a scaffold sequence for dCas9 binding and an approximately 20 nucleotide spacer that defines the genomic target of the sgRNA. Guide RNAs can be 2-part guide RNAs (crRNA+tracerRNA) or single guide RNA. One can change the genomic target of the gRNA-dCas9 complex by changing the spacer in the gRNA.

Exemplary α-Proteobacteria are those listed above such as *Z. mobilis*. Exemplary γ-Proteobacteria are those listed above.

Exemplary α-Proteobacteria and γ-Proteobacteria genes include essential metabolic genes, stress response genes, and stress resistance genes, such as pdc, hpnC, hpnH, hpnI, shc2, and hpnF.

In an aspect, the gRNA perfectly matches the α-Proteobacteria or γ-Proteobacteria gene, or wherein the gRNA has a mismatch with the α-Proteobacteria or γ-Proteobacteria gene. A perfect match can provide a complete knockdown of the gene, which a partial mismatch can provide reduced expression. The sequence of the gRNA can be modified to provide a desired level of expression of the α-Proteobacteria or γ-Proteobacteria gene. Thus, the Mobile-CRISPRi plasmids provide programmable, inducible, and titratable control over expression of all genes, including essential genes. By systematically introducing mismatches between gRNA spacers and target genes, knockdown gradients suitable for studying essential gene function can be produced.

In another aspect, a population of Mobile-CRISPRi plasmids is provided. Each individual species of the population comprises a gRNA library member comprising a unique gRNA spacer sequence. Strains comprising knockdown gradients of metabolic genes can be pooled and tested under a variety of growth conditions with fitness measured by next generation sequencing of the gRNA spacers.

In a further aspect, a method of partially or fully knocking down expression of a gene in α-Proteobacteria or γ-Proteobacteria comprises transferring the Mobile-CRISPRi plasmid described above into the α-Proteobacterium or γ-Proteobacterium and expressing the dCas9 protein and the gRNA.

In another aspect, a method of making an α-Proteobacteria or γ-Proteobacteria strain comprising a chromosomally inserted Mobile-CRISPRi expression cassette comprises triparental mating a first *E. coli* donor strain and a second *E. coli* donor strain and an α-Proteobacteria or γ-Proteobacteria recipient, wherein the first *E. coli* donor strain comprises a plasmid encoding a Tn7 transposase wherein the second *E. coli* donor strain comprises a Tn7 transposon encoding the Mobile-CRISPRi expression cassette, and wherein the Mobile-CRISPRi expression cassette comprises an expression cassette for a dCas9 protein, the dCas9 protein expressed with a strong α-Proteobacteria or γ-Proteobacteria ribosome binding site; and a gRNA expression cassette under control of the synthetic inducible promoter described above, wherein a gRNA-dCas9 complex produced from the Mobile-CRISPRi plasmid partially or fully blocks expression of an α-Proteobacteria or γ-Proteobacteria gene; and producing the α-Proteobacteria or γ-Proteobacteria strain comprising the chromosomally inserted Mobile-CRISPRi expression cassette.

The invention is further illustrated by the following non-limiting examples.

EXAMPLES

Methods

Strains and growth conditions. Strains are listed in Table 1. *Escherichia coli* was grown in LB broth, Lennox Sigma-Aldrich™ (BD240230; 10 g tryptone, 5 g yeast extract, 5 g NaCl per liter) at 37° C. aerobically in a flask with shaking at 250 rpm, in a culture tube on a roller drum, or in a 96 well deepwell plate with shaking at 200 rpm. *Z. mobilis* was grown in DSMZ medium 10 (10 g peptone and 10 g yeast extract per liter plus 2% glucose) at 30° C. aerobically without shaking. Media was solidified with 1.5% agar for growth on plates. Antibiotics were added when necessary: *E. coli* (100 µg/ml ampicillin, 20 µg/ml chloramphenicol, 50 µg/ml kanamycin) and *Z. mobilis* (100 µg/ml chloramphenicol, 120 µg/ml kanamycin). Diaminopimelic acid (DAP) was added at 300 µM to support growth of dap-*E. coli* strains. 0.1-1 mM Isopropyl β-d-1-thiogalactopyranoside (IPTG) was added where indicated. All strains were preserved in 15% glycerol at −80° C.

Plasmid construction. Plasmids and construction details are listed in Table 2. pir-dependent plasmids were propagated in *E. coli* strain BW25141 (sJMP146) and other plasmids in *E. coli* strain DH10B (sJMP006). Plasmids were assembled from fragments (linearized vector, PCR products, and/or synthetic DNA) using the NEBuilder® Hifi DNA assembly kit (New England Biolabs® (NEB) E2621). Plasmids were cut with restriction enzymes from NEB. Linearized plasmids were re-ligated using T4 DNA ligase (NEB M0202). Fragments were amplified using Q5 DNA polymerase (NEB 0491) followed by digestion with DpnI. Fragments were purified using the Monarch R PCR & DNA Cleanup Kit (NEB T1030) after digestion or amplification. Plasmids were transformed into electrocompetent *E. coli* cells using a BioRad Gene Pulser Xcell™ on the EC1 setting. Plasmids were purified using the GeneJET™ Plasmid Miniprep kit (Thermo K0503) or the Purelink™ HiPure Plasmid Midiprep kit (Invitrogen™ K210005). Site-directed mutagenesis of plasmids was performed by DNA synthesis with 2.5 U PfuUltra™ II Fusion HS DNA Polymerase (AgilentR), 0.2 µM oligonucleotide encoding the change, 0.2 mM dNTPs, and 50) ng of plasmid DNA in a 25-µL reaction with a 1-min/kb extension time at 68° C., followed by DpnI digestion. sgRNA-encoding sequences were cloned into CRISPRi plasmids between the BsaI sites with inserts prepared by one of two methods. In method one, two 24 nt oligonucleotides were designed to overlap such that when annealed, they have ends that are complementary to the BsaI-cut ends on the vector. Oligos (2 µM each) were annealed in 1× CutSmart R buffer (NEB) at 95° C. for 5 min followed by cooling to room temperature. For method two, fragments were amplified by PCR with primers oJMP197 and oJMP198 from a 78 nt oligonucleotide followed by digestion with BsaI-HF-v2 and purification with the Monarch R DNA purification kit (NEB) following the manufacturer's oligonucleotide purification protocol. Inserts (2 µl of a 1:40 dilution of annealed oligos or 2 ng purified digested PCR product) were ligated into 50 ng BsaI-digested vector. Oligonucleotides and synthetic DNA gBlocks were purchased from Integrated DNA Technologies® (Coralville, IA). Sequencing was performed by Functional Biosciences™ (Madison, WI). (Banta, A B et al., 2020, A High-Efficacy CRISPR Interference System for Gene Function Discovery in *Zymomonas mobilis*. Applied and Environmental Microbiology 86, No. 23). Plasmids and their sequences were deposited with Addgene (Addgene identification numbers 160073 to 160080).

Transfer of CRISPRi system to E. coli and Z. mobilis. Strains with a chromosomally-located CRISPRi expression cassette were constructed by tri-parental mating of two donor strains—one with a plasmid encoding Tn7 transposase and another with a plasmid containing a Tn7 transposon encoding the CRISPRi system—and a recipient strain (either E. coli BW25113 or Z. mobilis ZM4 (PK15436)). Briefly, all matings used E. coli WM6026 which is pir to support pir-dependent plasmid replication, dap⁻ making it dependent on diaminopimelic acid (DAP) for growth and encodes the RP4 transfer machinery required for conjugation. Donor strains were grown ~16 h at 37° C. in LB+100 µg/ml ampicillin and 300 µM DAP. E. coli recipient was grown ~16 h at 37° C. in LB. Z. mobilis recipient was grown ~24-30 h at 30° C. in DSMZ10. Cells were centrifuged at 4000×g for 5 min and gently resuspended twice in an equal volume of fresh medium with no antibiotic or DAP. For E. coli recipients, 700 µl LB, and 100 µl each donor and recipient were mixed in a sterile 1.5 ml microfuge tube. For Z. mobilis recipients, 200 µl DSMZ10, 500 µl Z. mobilis, 200 µl transposase donor and 100 µl transposon donor were mixed in a sterile 1.5 ml microfuge tube. Cells were centrifuged at 4000×g for 3 min, gently resuspended in 25 µl LB or DSMZ10, and pipetted onto a 13 mm cellulose filter, placed on prewarmed agar plate (LB for E. coli or DSMZ10 for Z. mobilis). Plates were incubated at 37° C. for 2-6 h for E. coli and 30° C. for 24 h for Z. mobilis. After the incubation period, using sterile forceps, filters were placed into sterile 1.5 ml microfuge tubes containing 200 µl sterile 1×PBS, vortexed 20 s to dislodge cells from filters, diluted in 1×PBS and plated on appropriate medium for recipient and antibiotic to select for transposon (see above) with no DAP (to select against the donor). Efficiency of transposition was generally ~1 in 103 for E. coli and ~1 in 105-106 for Z. mobilis. Isolated colonies were generally obtained from ~10-100 µl of 1:100 dilution per plate and isolated colonies were restruck for isolation to ensure purity.

CRISPRi insertion onto Z. mobilis chromosome. Insertion of the CRISPRi expression cassette into the Tn7att site downstream of glmS in Z. mobilis was confirmed by PCR with primers oJMP057 and oJMP058 (flanking insertion site) and oJMP059 and oJMP060 (upstream of insertion site and within CRISPRi transposon).

CRISPRi stability in Z. mobilis. Z. mobilis strains with chromosomally-located CRISPRi expression cassettes (6 individual isolates) were grown in liquid culture medium with antibiotic selection to saturation. This culture was serially diluted $10^{-5}$ into non-selective medium (starting OD $A_{600}$ ~0.00002) and grown ~17 generations back to saturation (OD $A_{600}$ ~2.0). Dilution and growth were repeated 2 additional times for a total of ~50 generations prior to plating on non-selective plates. Forty-eight isolated colonies were selected and patched on selective and non-selective plates and all strains retained the ability to grow on the antibiotic whose resistance was conferred by the chromosomally-located CRISPRi expression cassette.

GFP/RFP knockdown assays. GFP or RFP knockdown was measured using a plate reader (Tecan Infinite® 200 Pro M Plex). Cell density was determined by absorbance at 600 nm ($A_{600}$) and fluorescence was measured by excitation/emission at 482/515 nm for GFP and 555/584 nm for RFP. Initial cultures (n=4) were grown from single colonies to saturation (~30 h for Z. mobilis or ~16 h for E. coli) in 1 ml medium in 96 well deepwell plates. These cultures were serially diluted 1:1000 (Z. mobilis) or 1:10,000 (E. coli) into 1 ml fresh medium (no antibiotic and 0-1 mM IPTG as indicated) and grown back to saturation (~24-30 h for Z. mobilis or ~8-16 h for E. coli). Pelleted cells were resuspended in 1 ml 1×PBS, diluted if necessary, and 200 µl was transferred to a clear bottom black microtiter plate and measured in the plate reader as indicated above. Fluorescence values were normalized to cell density and to measurements from strains not expressing GFP.

Gene knockdown spot dilution assay. Z. mobilis strains with chromosomally-located CRISPRi expression cassettes (2 individual isolates) were grown in liquid culture medium with antibiotic selection to saturation. These cultures were serially diluted 1:10 in non-selective medium and 3 µl was spotted onto plates containing 0, 0.1 mM or 1 mM IPTG which were incubated at 30° C. aerobically prior to analysis.

Gene knockdown growth assay. Z. mobilis strains with chromosomally-located CRISPRi expression cassettes (n=2 individual isolates) were grown in liquid culture medium with antibiotic selection to saturation. These cultures were serially diluted 1:1000 into non-selective medium with 0 or 0.1 mM IPTG and 0, 0.63%, 1.25% or 2.5% isobutanol in a 96 well deepwell plate and incubated at 30° C. aerobically prior to analysis of growth (measured as absorbance at 600 nm ($A_{600}$)).

TABLE 1

STRAINS

| Number | Description[a] |
|---|---|
| sJMP146 | Escherichia coli (pir+ cloning strain) (BW25141) Δ(araD-araB)567, ΔlacZ4787(::rrnB-3), Δ(phoB-phoR) λ-, galU95, ΔuidA3::pir+, recAl, endA9(Δ-ins)::FRT, rph-1, Δ(rhaD-rhaB)568, hsdR514 |
| sJMP412 | Zymomonas mobilis, ZM4, ΔhsdSc (ZMO1933), Δmrr (ZMO0028), ΔhsdSr (pZM32_028), Δcas3(ZMO0681), (strain PK15436) |
| sJMP424 | Escherichia coli (pir+ dap⁻ mating strain) (strain WM6026) lacIq, rrnB3, DElacZ4787, hsdR514, DE(araBAD)567, DE(rhaBAD)568, rph-1 att-lambda::pAE12-del (oriR6K/cat::frt5), Δ4229(dapA)::frt(DAP−), Δ(endA)::frt, uidA(ΔMluI)::pir(wt), attHK::pJK1006:: Δ½(ΔoriR6K-cat::frt5, ΔtrfA::frt) |

[a]WT, wild type; Cm', chloramphenicol resistance cassette; Amp', ampicillin resistance cassette; Kan', kanamycin resistance cassette; Spec', spectinomycin resistance cassette; MCi, Mobile-CRISPRi; RFP, red fluorescent protein; vA to vF, sgRNA promoter variants; sfGFP, superfolder GFP.

TABLE 2

PLASMIDS

| Plasmid | Description[a] | Construction/notes | marker[b] |
|---|---|---|---|
| pJMP2093 | MCi-vB-GFP_BsaI | pJMP2046 cut with EcoRI assembled with gBlock oJMP191 | amp[r], cm[r] |
| pJMP2095 | MCi-vB-GFP_gfp | pJMP2048 cut with EcoRI assembled with gBlock oJMP192 | amp[r], cm[r] |
| pJMP2132 | MCi-vB_BsaI | pJMP2092 cut with PmeI and re-ligated to remove sfGFP | amp[r], cm[r] |
| pJMP2367 | MCi-vC-GFP_BsaI | Assemble EcoRI-cut pJMP2093 with gBlock oJMP347 | amp[r], cm[r] |
| pJMP2369 | MCi-vD-GFP_BsaI | Assemble EcoRI-cut pJMP2093 with gBlock oJMP348 | amp[r], cm[r] |
| pJMP2371 | MCi-vE-GFP_BsaI | Assemble EcoRI-cut pJMP2093 with gBlock oJMP349 | amp[r], cm[r] |
| pJMP2373 | MCi-vF-GFP_BsaI | Assemble EcoRI-cut pJMP2093 with gBlock oJMP350 | amp[r], cm[r] |
| pJMP2375 | MCi-vC-GFP_gfp | Assemble EcoRI-cut pJMP2093 with gBlock oJMP351 | amp[r], cm[r] |
| pJMP2377 | MCi-vD-GFP_gfp | Assemble EcoRI-cut pIMP2093 with gBlock oJMP352 | amp[r], cm[r] |
| pJMP2379 | MCi-vE-GFP_gfp | Assemble EcoRI-cut pIMP2093 with gBlock oJMP353 | amp[r], cm[r] |
| pJMP2381 | MCi-vF-GFP_gfp | Assemble EcoRI-cut pJMP2093 with gBlock oJIMP354 | amp[r], cm[r] |

[a]MCi, Mobile-CRISPRi; ICE, integrative conjugative element; Hsa, *Homo sapiens* codon-optimized dCas9; vA to vF, sgRNA promoter variants; RFP, red fluorescent protein; GFP, green fluorescent protein; BsaI, vector with BsaI cloning site for sgRNA.
[b]Cm[r], chloramphenicol resistance; Amp[r], ampicillin resistance, Kan[r], kanamycin resistance

Example 1: Optimization of CRISPRi for *Z. mobilis*

To establish Spy dCas9-based CRISPRi in *Z. mobilis*, we first attempted to deliver a previously described, Tn7-based Mobile-CRISPRi "test" vector containing the gene encoding monomeric Red Fluorescent Protein (mRFP) and an sgRNA targeting mRFP to wild-type *Z. mobilis* strain ZM4 via conjugation. We failed to obtain transconjugants with wild-type but succeeded at integrating Mobile-CRISPRi into the genome of a restriction deficient derivative strain, consistent with Mobile-CRISPRi vectors containing multiple predicted recognition sites for *Z. mobilis* restriction enzymes (sJMP412, Lal et al., 2021, Applied and Environmental Microbiology 87, No. 19). Thus, we used the restriction-deficient strain in all subsequent experiments (Table 1). We next used a fluorimeter to measure CRISPRi knockdown of mRFP at saturating concentrations of inducer (1 mM IPTG), finding poor knockdown (2.4-fold); although our measurements were complicated by the weak fluorescence of mRFP in *Z. mobilis*. Mobile-CRISPRi inserted into the *Z. mobilis* genome downstream of glmS as expected (FIG. 2) and was stable over 50 generations of growth in rich medium without selection.

Figure 5:
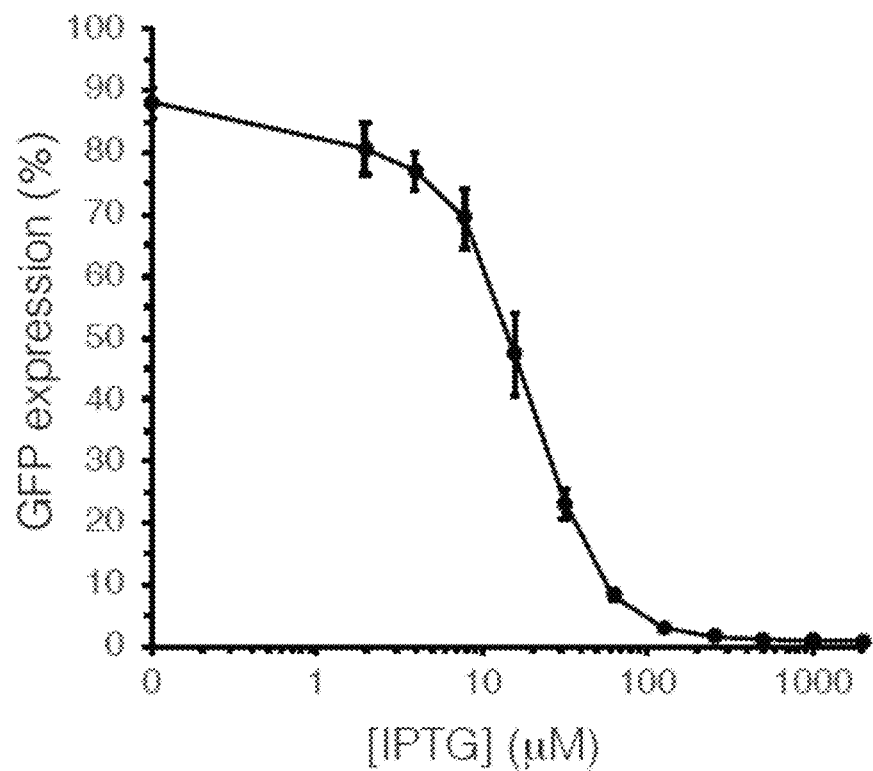
FIG. 5 shows expression of Z. mobilis CRISPRi system is inducible over a range of IPTG concentrations.

To optimize CRISPRi function and improve knockdown detection, we took advantage of the modularity of Mobile-CRISPRi (FIG. 1) to swap in biological "parts" that have been confirmed to function in *Z. mobilis*. We replaced mRFP with a gene encoding superfolder GFP (sfGFP), expressed dcas9 with a "strong" *Z. mobilis* ribosome binding site from a T7A1-derived promoter, and expressed an sgRNA targeting sfGFP from the lacUV5 promoter (i.e., promoter A; FIG. 3, Table 4). This CRISPRi system showed strong knockdown (20-fold) of sfGFP at saturating inducer, but also considerable leakiness without inducer (FIG. 3, promoter A). A similar system-except containing a symmetric lac operator that binds LacI more tightly than wild-type operators inserted into the lacUV5 promoter spacer (FIG. 3, promoter B)-showed no detectable leakiness but only modest knockdown (10-fold; FIG. 4), suggesting that the concentration of either dCas9 or the sgRNA was limiting for knockdown. To determine the limiting factor, we expressed either the sfGFP sgRNA or dcas9 from a multicopy plasmid in the context of CRISPRi with promoter B, finding that sgRNA expression was primarily limiting knockdown (data not shown). Because lacUV5 has the highest confirmed activity of any promoter measured in *Z. mobilis* and because no consensus sequence exists in the literature for native *Z. mobilis* promoters, we built LacI-regulated synthetic promoters based on *Escherichia coli* σ[70] consensus elements that we reasoned could increase sgRNA expression to a higher level than lacUV5 (Table 3, promoters C-F). All four synthetic promoters improved the knockdown properties of *Z. mobilis* CRISPRi, but promoter C—which features consensus UP and −10 elements with a near consensus −35 and an ideal spacer length (Table 4)—provided the best combination of strong knockdown (125-fold) and negligible leakiness (~10-15%; FIG. 4). Using CRISPRi with promoter C, we found that intermediate inducer concentrations enabled titration of knockdown activity (FIG. 5). We conclude that Mobile-CRISPRi optimized for *Z. mobilis* is efficacious, inducible, and titratable.

TABLE 3

PROMOTERS- OPTIMIZATION OF SGRNA EXPRESSION.
SIX PROMOTER SEQUENCES (A-F) BASED ON EITHER
LACUV5 OR A SYNTHETIC PROMOTER WERE INCORPORATED
INTO THE CRISPRI SYSTEM.

| | SEQ ID NO: | Parent promoter | lac operator | Up element | −10/−35 spacer |
|---|---|---|---|---|---|
| A | 1 | lacUV5 | (none) | − | 18 |
| B | 2 | lacUV5 | symmetric | − | 18 |
| C | 3 | synthetic | symmetric | + | 17 |
| D | 4 | synthetic | O1 | + | 17 |

TABLE 3-continued

PROMOTERS- OPTIMIZATION OF SGRNA EXPRESSION.
SIX PROMOTER SEQUENCES (A-F) BASED ON EITHER
LACUV5 OR A SYNTHETIC PROMOTER WERE INCORPORATED
INTO THE CRISPRI SYSTEM.

| | SEQ ID NO: | Parent promoter | lac operator | Up element | −10/−35 spacer |
|---|---|---|---|---|---|
| E | 5 | lacUV5 | symmetric | + | 18 |
| F | 6 | lacUV5 | O1 | + | 18 |

The −10 and −35 core promoter elements are underlined and shown in bold. See also FIG. 3.

Example 2: Mismatch-CRISPRi Enables Knockdown Gradients in Z. mobilis

Figure 6:
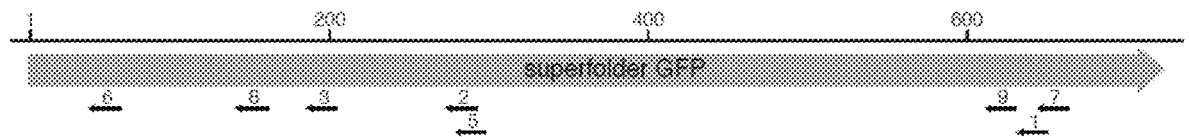
FIG. 6 shows variable repression using mismatch sgRNAs in the Z. mobilis Mobile-CRISPRi system. Location of sgRNA target on the GFP gene is shown. Scale bar indicates nucleotides.
Figure 7:
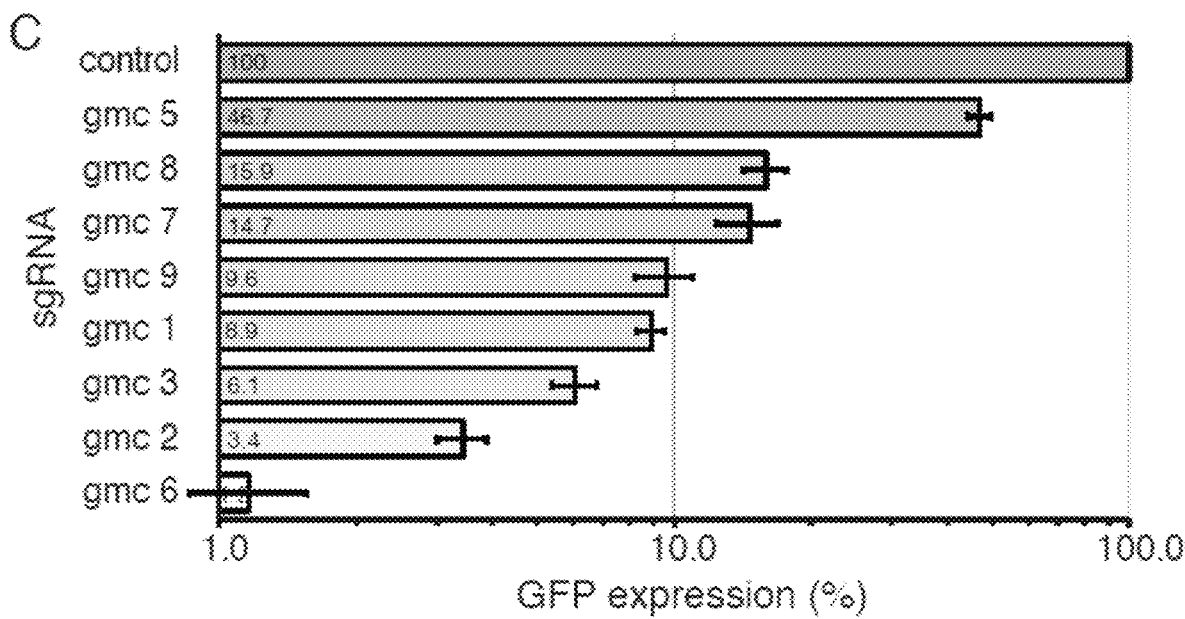
FIG. 7 shows the knockdown of GFP expression in Z. mobilis CRISPRi expression strains with mismatch sgRNAs. Control indicates a non-targeting sgRNA.

The relationship between fitness and gene expression varies by gene and is generally unknown. This relationship is especially important to consider for essential genes, which have a fitness of zero at full knockdown, but a large range of possible fitness values at intermediate levels of knockdown depending on the function of the gene product. Excessive knockdown of essential genes results in strains that grow poorly and are difficult to phenotype. Recent work has shown that systematically introducing mismatches between sgRNA spacers and target genes can generate knockdown gradients suitable for studying essential gene function; we call this strategy, "Mismatch-CRISPRi". Mismatch-CRISPRi functions in mammalian cells and diverse model bacteria (i.e., E. coli and B. subtilis), but has not been demonstrated in α-Proteobacteria. To test Mismatch-CRISPRi in Z. mobilis, we cloned a set of mismatched sgRNAs to target sfGFP into our Z. mobilis CRISPRi system with sgRNA promoter C (FIG. 6 and Table 4). Using these mismatched guides, we were able to generate a knockdown gradient of sfGFP that spanned nearly two orders of magnitude and contained multiple sgRNAs that caused intermediate knockdown levels at saturating inducer (FIG. 7). Further, we introduced our Z. mobilis Mismatch-CRISPRi vectors into E. coli permitting a direct comparison of sfGFP knockdown in the two divergent species (data not shown). Consistent with a previous comparison between E. coli and B. subtilis, we found excellent agreement between sfGFP knockdown gradients in E. coli and Z. mobilis ($R^2=0.8$). This demonstrates the broad utility of Mismatch-CRISPRi to predictably generate partial knockdowns and shows that Z. mobilis CRISPRi is robust to genetic background and may function well in multiple species.

TABLE 4

SGRNAS

| | sgRNA 5'-3' | SEQ ID NO: |
|---|---|---|
| gmc5 | GCGUUCCUGUACAUAACCcU | 47 |
| gmc8 | AGUAGUGCAAAgAAAUUUAA | 48 |
| gmc7 | AUGUuGUCACGCUUUUCGUU | 49 |
| gmc9 | AAcGACAGAUUGUGUCGAC | 50 |
| gmc1 | UUcCGUUGGGAUCUUUCGAA | 51 |
| gmc3 | GUCAGAGUAGUGuCAAGUGU | 52 |
| gmc2 | uaGUACAUAACCUUCGGGCA | 53 |
| gmc6 | CAUCUAAUUCAACAAGAAUU seed | 54 |

Example 3: Z. mobilis CRISPRi Targets Essential Genes

To examine the efficacy of Z. mobilis CRISPRi in characterizing essential gene function, we first targeted rpIL (ZM00728)—an essential gene encoding the universally conserved ribosomal protein, L12—as a positive control. We found a greater than six orders of magnitude reduction in plating efficiency for strains expressing an rpIL sgRNA versus a control strain expressing a non-targeting sgRNA at saturating inducer (FIG. 8 panel A), indicating substantial loss of cell viability and relatively low levels of suppressor mutations that inactive the CRISPRi system. Based on these results, we conclude that Z. mobilis CRISPRi is effective at assessing gene essentiality.

Figure 8:
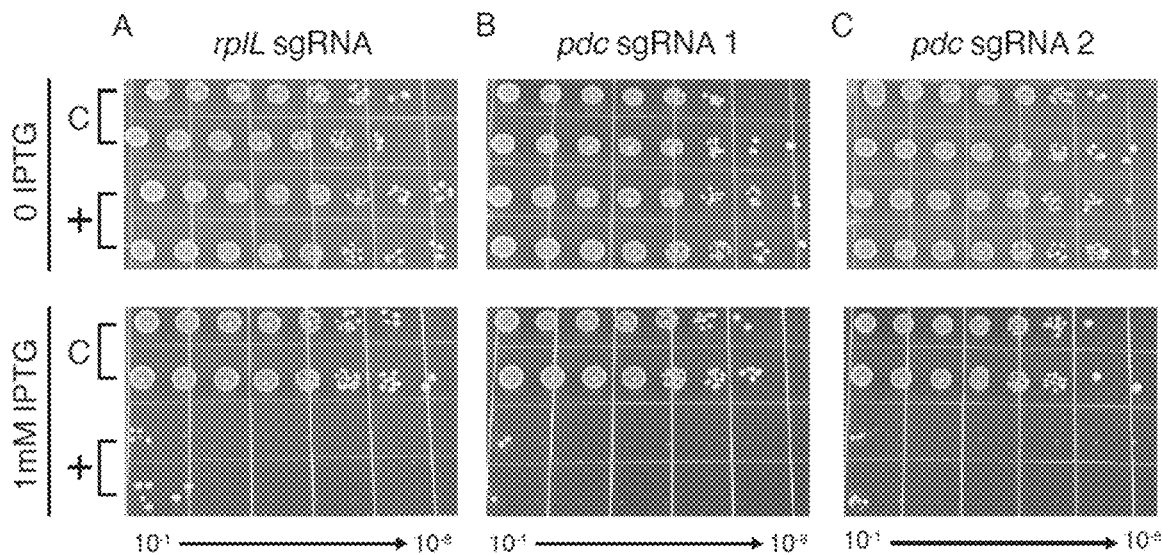
FIG. 8 shows CRISPRi knockdown of endogenous essential genes. Z. mobilis strains with CRISPRi cassettes encoding sgRNAs targeting essential genes pdc and rpIL were serially diluted 1:10 ($10^{-1}$ through $10^{-8}$) and spotted on agar plates with either 0 or 1 mM IPTG. C indicates a non-targeting sgRNA.

Pyruvate decarboxylase, encoded by the pdc gene (ZMO1360), is a key metabolic enzyme in Z. mobilis that converts pyruvate into acetaldehyde—the penultimate step in ethanol production. Despite its important role in fermentation of sugars to ethanol, the Z. mobilis literature is conflicted about whether pdc is essential or dispensable in aerobic conditions. To determine the essentiality of pdc, we used Z. mobilis CRISPRi with promoter C and an sgRNA targeting the 5' end of the pdc coding sequence. We found a greater than six orders of magnitude loss in plating efficiency for the pdc knockdown strain at saturating inducer (FIG. 7 panel B); this result was indistinguishable from the loss of fitness observed when we targeted rpIL, suggesting that pdc is essential for aerobic growth. To confirm that our result was not due to off-target effects of CRISPRi, we tested a second, non-overlapping sgRNA targeting pdc, finding the same results (FIG. 8 panel C). We conclude that pdc is essential for aerobic growth of Z. mobilis.

Figure 9:
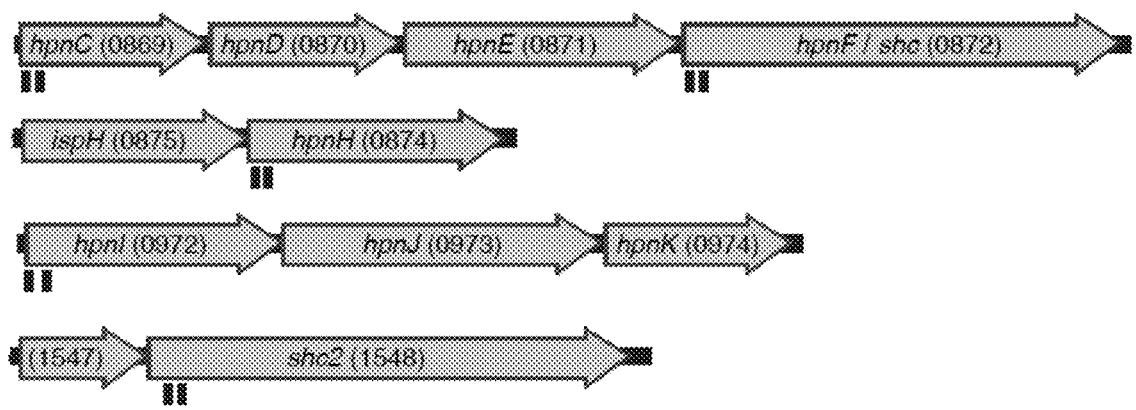
FIG. 9 shows CRISPRi knockdown of hopanoid lipid synthesis related genes. Z. mobilis strains were constructed with CRISPRi cassettes encoding sgRNAs targeting genes in hopanoid synthesis operons (and a non-targeting control). The number of the ZMO tag is in parentheses after the gene name. Target position of sgRNAs on targeted genes (hpnC, hpnF, hpnH, hpnI, shc2) are shown in black under the genes.
Figure 10:
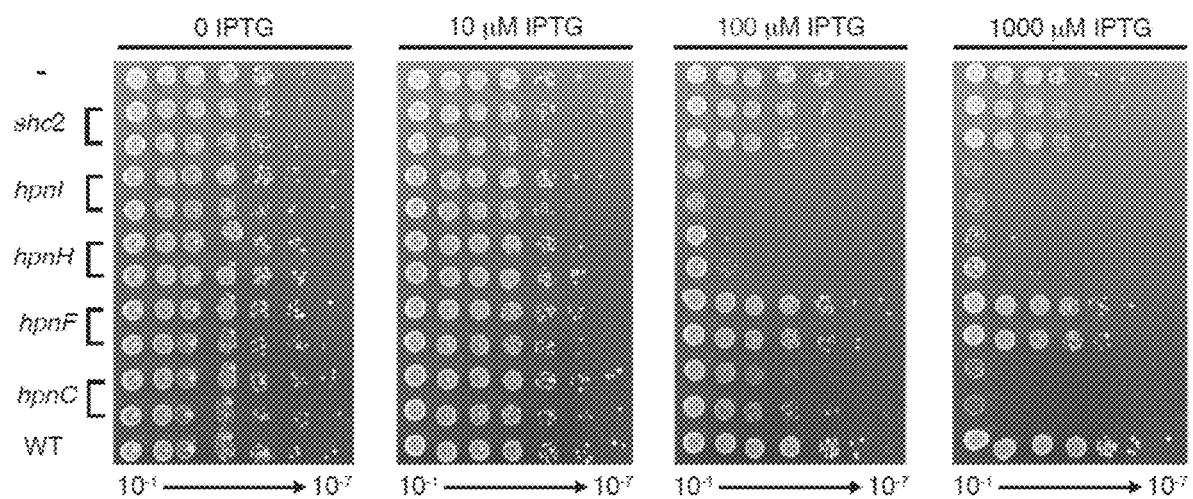
FIG. 10 shows strains were serially diluted 1:10 ($10^{-2}$ through $10^{-8}$) and spotted on agar plates with either 0, 0.1, or 1 mM IPTG. C indicates a non-targeting sgRNA.

Example 4: Essentiality and IBA Sensitivity Phenotypes of Hopanoid Biosynthesis Genes Genes encoding hopanoid biosynthesis enzymes (i.e., hpn/she genes; FIG. 9) are thought to be essential in Z. mobilis based on growth cessation caused by small molecule inhibitors of Squalene-hopene cyclase and the observation that strains with transposon insertions in hpn genes always also contain a wild-type copy of the gene. To further probe the essentiality of hopanoids, we targeted hpn/she genes using Z. mobilis CRISPRi with promoter B. Because CRISPRi blocks transcription of downstream genes in an operon (i.e., polarity), we chose to target the first hpn/she gene present in each operon (FIG. 9 genes with indicated target positions). We found considerable defects in plating efficiency for strains with sgRNAs targeting hpn ((ZMO0869), hpnH (ZMO0874), and hpnI (ZMO0972), consistent with a requirement of hopanoid synthesis for growth (FIG. 10). In contrast, targeting the hpnI (a.k.a., shc1; ZMO0872) and shc2 (ZMO1548) genes that both encode Squalene-hopene cyclase had no effect on plating efficiency, suggesting that they are functionally redundant under the conditions tested.

Figure 11:
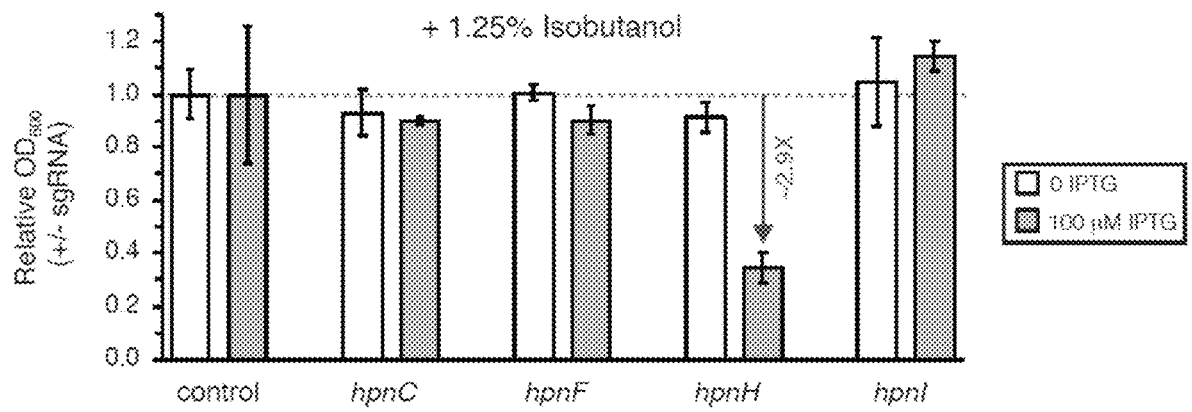
FIG. 11 shows strains were diluted 1:1000 and grown in liquid culture, aerobically in the presence of 1.25% isobutanol and 0 or 0.1 mM IPTG ~10 doublings prior to measurement of cell density (OD $A_{600}$). Growth measurements were normalized to a strain expressing a non-targeting sgRNA. Standard deviation between 4 replicates is shown. Arrow indicates fold change compared to control.

Classic studies of *Z. mobilis* physiology and contemporary work using hpn+/hpn::Tn strains have linked hopanoid production and ethanol resistance; however, it is unknown if hopanoids provide resistance to advanced biofuels, such as IBA. To examine the relationship between hpn/she genes, we first determined the concentration of IBA needed to partially inhibit growth of *Z. mobilis* in sealed, deep 96 well plates. We found that addition of 1.25% v/v IBA to rich medium inhibited *Z. mobilis* growth by ~50% (data not shown). We then grew our CRISPRi strains targeting hpn/she operons with a subsaturating concentration of inducer (100 µM IPTG) for a limited number of generations in the presence or absence of IBA. Under these conditions, hpnH was the only knockdown tested that showed increased sensitivity to IBA, with a 2.9-fold reduction in final $OD_{600}$ at the end of the growth period relative to a non-targeting control sgRNA strain (FIG. 11). HpnH adds an extended side chain to the core hopanoids, diploptene and diplopterol (data not shown), suggesting that buildup of core hopanoids may compromise IBA tolerance in *Z. mobilis*. We conclude that hopanoid biosynthesis operons are essential in *Z. mobilis*, but production of extended hopanoids may not be involved in IBA tolerance.

Discussion

The lack of genetic tools for bioenergy relevant, non-model bacteria has slowed progress toward engineering efficient production strains for advanced biofuels, such as IBA. The CRISPRi system for *Z. mobilis* described herein overcomes this obstacle by enabling programmable, inducible, and titratable control over expression of all genes. Because *Z. mobilis* CRISPRi also functions well in the distantly-related bacterium, *E. coli*, the system as constructed may have broad utility across species, including other bioenergy-relevant α-Proteobacteria. Mobile-CRISPRi for *Z. mobilis* has taught us valuable lessons that should be generalizable across species: first, identify limiting components (either dCas9 or sgRNAs) by overexpression, and second, design strong synthetic promoters that take advantage of conserved interactions between RNA polymerase holoenzyme and DNA to improve portability.

CRISPRi is an ideal genetic tool to take advantage of the unusual properties of *Z. mobilis*. Because many metabolic genes are predicted to be essential, controlling metabolic flux may entail constructing strains with partial knockdowns of essential genes. Mismatch-CRISPRi libraries are particularly well suited for empirically defining relationships between knockdown of metabolic genes (and associated changes in flux) with fitness, as strains comprising knockdown gradients of metabolic genes can be pooled and tested under a variety of growth conditions with fitness measured by next generation sequencing of sgRNA spacers. Further, the *Z. mobilis* chromosome is possibly polyploid, or is at least capable of duplicating at high frequency; this can cause problems with deletion/transposon insertion analysis of essential genes or other genes that have a strong impact on fitness when disrupted. For instance, a high-throughput analysis of isolated transposon insertion mutants revealed that there was no significant difference in the probability of a transposon inserting a predicted essential versus non-essential gene, suggesting a polyploid chromosome and underscoring issues with interpreting insertion/deletion results in *Z. mobilis*. In contrast, CRISPRi is largely unaffected by polypoidy—it is capable of targeting essential genes across multiple copies of the chromosome as long as the sgRNA-dCas9 complex is expressed at high enough levels to account for multiple targets.

Numerous studies have linked hopanoid production and ethanol tolerance in *Z. mobilis*, but whether hopanoids provide resistance to non-physiological alcohols, such as IBA, remains unclear. Our CRISPRi results suggest that high concentrations of extended hopanoids present in wild-type *Z. mobilis* do not impart IBA resistance, but instead that preventing hopanoid extension by blocking hpnH expression causes sensitivity. The simplest explanation for these results is that core (i.e., unextended) hopanoids, diploptene and diplopterol, accumulate in the cell and negatively impact the outer membrane.

The CRISPRi system opens the door to high-throughput, systematic analysis of gene function in *Z. mobilis*. We envision that such screens will be invaluable for identifying genes involved in resistance to hydrolysate or biofuel inhibitors, genetic fingerprinting of hydrolysates from different plant sources or environments and improving our understanding of the unique metabolism of *Z. mobilis*. We anticipate that this information will power the next generation of biofuel production strains, resulting in higher yields of advanced biofuels and bioproducts.

Example 5: Promoter C in *Acinetobacter baumannii*

Figure 12:
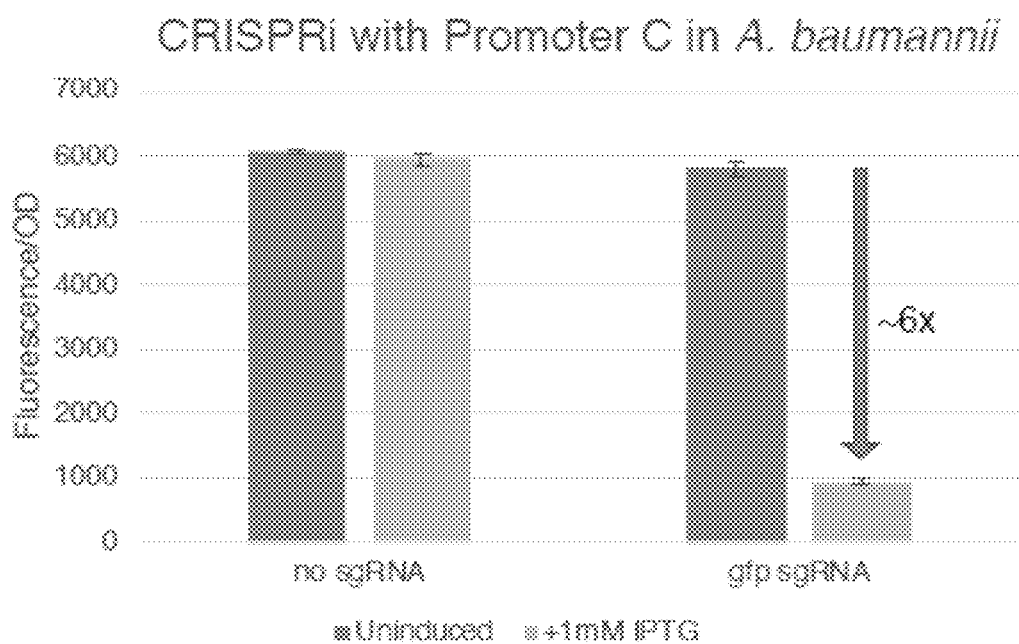
FIG. 12 shows the expression of the CRISPRi system in A. baumannii.

We tested the function of promoter C in *A. baumannii* by using it to express an sgRNA targeting sfGFP in the context of Mobile-CRISPRi. Weak expression of dcas9 in our setup limited the overall knockdown, but we were still able to detect ~6× knockdown (FIG. 12); this indicates that promoter C is functional in *A. baumannii*. The assay we used to quantify sfGFP knockdown is identical to the one described for *Z. mobilis*, except that *A. baumannii* was grown at 37° C. in LB medium, and the initial dilution of overnight cells prior to induction of CRISPRi was 1:10,000.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. "About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±10% or 5% of the stated value. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

All references cited herein are hereby incorporated, in their entirety, by reference thereto.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

roteobacteria strain.

The invention claimed is:

1. A synthetic inducible proteobacterial promoter comprising

5'-(UP element)-(−35 element)-(spacer element)-(−10 element)-(discriminator element)-3'; wherein the (UP element) is SEQ ID NO: 14 or SEQ ID NO: 15;

the (−35 element) is TTTACA, TTGAAA, TTGAAT, or TTTAAA;

the (spacer element) is ATTGTGAGCGCTCACAAT (SEQ ID NO: 11), TTGTGAGCGCTCACAAT (SEQ ID NO: 12), or TGTGAGCGGATAACAAT (SEQ ID NO: 13);

the (−10 element) is TATAAN$_{26}$ wherein N$_{26}$ is A, C, G or T; and the (discriminator element) is GTCTAGT or TCTAGT, wherein the synthetic inducible promoter is inducible with isopropyl β-d-1-thiogalactopyranoside (IPTG), or lactose in proteobacteria strain, wherein the proteobacteria strain is *Zymomonas mobilis* or *Acinetobacter baumanii*.

2. The synthetic inducible promoter of claim 1, that is Promoter C (SEQ ID NO: 3), Promoter D (SEQ ID NO: 4), Promoter E (SEQ ID NO: 5) or Promoter F (SEQ ID NO: 6).

3. A vector comprising the synthetic inducible promoter of claim 1.

4. A proteobacteria strain comprising the inducible promoter of claim 1, wherein the proteobacteria strain is *Zymomonas mobilis* or *Acinetobacter baumanii*.

5. The proteobacteria strain of claim 4, wherein the proteobacteria strain is *Zymomonas mobilis*.

6. A Mobile-CRISPRi plasmid, comprising, in operable communication,
an expression cassette for a dCas9 protein, the dCas9 protein expressed with an α-Proteobacteria or γ-Proteobacteria ribosome binding site; and
a gRNA expression cassette under control of the synthetic inducible promoter of claim 1,
wherein the spacer of the gRNA is fully matched or has a mismatch with a proteobacteria gene and wherein the gRNA-dCas9 complex produced from the Mobile-CRISPRi partially or fully blocks expression of the proteobacteria gene,
wherein the proteobacteria strain is *Zymomonas mobilis* or *Acinetobacter baumanii*.

7. The Mobile-CRISPRi plasmid of claim 6, wherein the synthetic inducible promoter is Promoter C (SEQ ID NO: 3), Promoter D (SEQ ID NO: 4), Promoter E (SEQ ID NO: 5), or Promoter F (SEQ ID NO: 6).

8. The Mobile-CRISPRi plasmid of claim 6, wherein the dCas9 is *Streptococcus pyogenes* dCas9, or a *Homo sapiens* optimized dCas9.

9. The Mobile-CRISPRi plasmid of claim 6, wherein the proteobacteria is *Zymomonas mobilis*.

10. The Mobile-CRISPRi plasmid of claim 6, wherein the proteobacteria gene is an essential metabolic gene, a stress response gene, or a stress resistance gene.

11. The Mobile-CRISPRi plasmid of claim 6, wherein the gRNA perfectly matches the proteobacteria gene.

12. A population of Mobile-CRISPRi plasmids of claim 6, wherein each individual species of the population comprises a gRNA library member comprising a unique gRNA spacer sequence.

13. A method of partially or fully knocking-down expression of a gene in proteobacteria, comprising transferring the Mobile-CRISPRi plasmid of claim 6 into the proteobacterium, and expressing the dCas9 protein and the gRNA, wherein the proteobacterium is *Zymomonas mobilis* or *Acinetobacter baumanii*.

14. The method of claim 13, wherein the proteobacterium is *Zymomonas mobilis*.

15. A method of making a proteobacteria strain comprising a chromosomally inserted Mobile-CRISPRi expression cassette, comprising triparental mating a first *E. coli* donor strain and a second *E. coli* donor strain and a proteobacteria recipient, wherein the first *E. coli* donor strain comprises a plasmid encoding a Tn7 transposase, wherein the second *E. coli* donor strain comprises a Tn7 transposon encoding the Mobile-CRISPRi expression cassette, and wherein the Mobile-CRISPRi expression cassette comprises an expression cassette for a dCas9 protein, the dCas9 protein expressed with a α-Proteobacteria or γ-Proteobacteria ribosome binding site; and a gRNA expression cassette under control of the synthetic inducible promoter of claim 1, wherein a gRNA-dCas9 complex produced from the Mobile-CRISPRi plasmid partially or fully blocks expression of a proteobacteria gene; and producing the proteobacteria strain comprising the chromosomally inserted Mobile-CRISPRi expression cassette, wherein the proteobacteria is *Zymomonas mobilis* or *Acinetobacter baumannii*.

16. The method of claim 15, wherein the proteobacteria strain is *Zymomonas mobilis*.

17. The method of claim 6, wherein the mismatched spacer of the gRNA has a one or two nucleotide mismatches with the proteobacteria gene.

* * * * *

SEQUENCE LISTING

```
<160> NUMBER OF SEQ ID NOS: 54

<210> SEQ ID NO 1
<211> LENGTH: 60
<212> TYPE: DNA
<213> ORGANISM: Artificial sequence
<220> FEATURE:
<223> OTHER INFORMATION: promoter

<400> SEQUENCE: 1
ctcactcatt aggcacccca ggctttacac tttatgcttc cggctcgtat aatgtctagt        60

<210> SEQ ID NO 2
<211> LENGTH: 60
<212> TYPE: DNA
<213> ORGANISM: Artificial sequence
<220> FEATURE:
<223> OTHER INFORMATION: promoter

<400> SEQUENCE: 2
ctcactcatt aggcacccca ggctttacaa ttgtgagcgc tcacaattat aatgtctagt        60

<210> SEQ ID NO 3
<211> LENGTH: 58
<212> TYPE: DNA
<213> ORGANISM: Artificial Sequence
<220> FEATURE:
<223> OTHER INFORMATION: Promoter

<400> SEQUENCE: 3
ggaaaatttt ttttcaaaag tacttgaaat tgtgagcgct cacaattata attctagt         58

<210> SEQ ID NO 4
<211> LENGTH: 58
<212> TYPE: DNA
<213> ORGANISM: Artificial Sequence
<220> FEATURE:
<223> OTHER INFORMATION: Promoter

<400> SEQUENCE: 4
ggaaaatttt ttttcaaaag tacttgaatt gtgagcggat aacaattata attctagt         58

<210> SEQ ID NO 5
<211> LENGTH: 59
<212> TYPE: DNA
<213> ORGANISM: Artificial  sequence
<220> FEATURE:
<223> OTHER INFORMATION: Promoter

<400> SEQUENCE: 5
ggaaaatttt ttttcaaaag tactttacaa ttgtgagcgc tcacaattat aattctagt        59
```

```
<210> SEQ ID NO 6
<211> LENGTH: 59
<212> TYPE: DNA
<213> ORGANISM: Artificial Sequence
<220> FEATURE:
<223> OTHER INFORMATION: Promoter

<400> SEQUENCE: 6
ggaaaatttt ttttcaaaag tactttaaat tgtgagcgga taacaattat aattctagt    59

<210> SEQ ID NO 7
<211> LENGTH: 58
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (1)..(23)
<223> OTHER INFORMATION: n is any nucleotide
<220> FEATURE:
<221> NAME/KEY: misc_feature
<222> LOCATION: (30)..(46)
<223> OTHER INFORMATION: n is any nucleotide
<220> FEATURE:
<221> NAME/KEY: misc_feature
<222> LOCATION: (43)..(58)
<223> OTHER INFORMATION: n is any nucleotide

<400> SEQUENCE: 7
nnnnnnnnnn nnnnnnnnnn nnnttgacan nnnnnnnnnn nnnnnntata atnnnnnn      58

<210> SEQ ID NO 8
<211> LENGTH: 23
<212> TYPE: DNA
<213> ORGANISM: Artificial Sequence
<220> FEATURE:
<223> OTHER INFORMATION: Promoter
<220> FEATURE:
<221> NAME/KEY: misc_feature
<222> LOCATION: (1)..(2)
<223> OTHER INFORMATION: n is any nucleotide
<220> FEATURE:
<221> NAME/KEY: misc_feature
<222> LOCATION: (5)..(5)
<223> OTHER INFORMATION: h is t, a, or c
<220> FEATURE:
<221> NAME/KEY: misc_feature
<222> LOCATION: (6)..(9)
<223> OTHER INFORMATION: w is t or a
<220> FEATURE:
<221> NAME/KEY: misc_feature
<222> LOCATION: (12)..(12)
<223> OTHER INFORMATION: n is any nucleotide
<220> FEATURE:
<221> NAME/KEY: misc_feature
<222> LOCATION: (13)..(13)
<223> OTHER INFORMATION: y is t or c
<220> FEATURE:
<221> NAME/KEY: misc_feature
<222> LOCATION: (14)..(16)
<223> OTHER INFORMATION: n is any nucleotide
<220> FEATURE:
<221> NAME/KEY: misc_feature
<222> LOCATION: (17)..(18)
<223> OTHER INFORMATION: w is t or a
<220> FEATURE:
<221> NAME/KEY: misc_feature
<222> LOCATION: (20)..(20)
<223> OTHER INFORMATION: s is c or g
<220> FEATURE:
<221> NAME/KEY: misc_feature
<222> LOCATION: (21)..(21)
<223> OTHER INFORMATION: b is c or g or t
<220> FEATURE:
```

```
<221> NAME/KEY: misc_feature
<222> LOCATION: (22)..(22)
<223> OTHER INFORMATION: v is c or a or g
<220> FEATURE:
<221> NAME/KEY: misc_feature
<222> LOCATION: (23)..(23)
<223> OTHER INFORMATION: n is any nucleotide

<400> SEQUENCE: 8
nnaahwwwwt tnynnnwwas bvn                                           23

<210> SEQ ID NO 9
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 9 gaaaatttt tttaaaaaaa aan                                            23

<210> SEQ ID NO 10
<211> LENGTH: 22
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (22)..(22)
<223> OTHER INFORMATION: n is any nucleotide

<400> SEQUENCE: 10
ttgctgctcg taaaaaaaaa an                                            22

<210> SEQ ID NO 11
<211> LENGTH: 18
<212> TYPE: DNA
<213> ORGANISM: Artificial sequence
<220> FEATURE:
<223> OTHER INFORMATION: Promoter

<400> SEQUENCE: 11
attgtgagcg ctcacaat                                                 18

<210> SEQ ID NO 12
<211> LENGTH: 17
<212> TYPE: DNA
<213> ORGANISM: Artificial sequence
<220> FEATURE:
<223> OTHER INFORMATION: Promoter

<400> SEQUENCE: 12
ttgtgagcgc tcacaat                                                  17

<210> SEQ ID NO 13
<211> LENGTH: 17
<212> TYPE: DNA
<213> ORGANISM: Artificial sequence
<220> FEATURE:
<223> OTHER INFORMATION: Promoter

<400> SEQUENCE: 13
tgtgagcgga taacaat                                                  17
```

```
<210> SEQ ID NO 14
<211> LENGTH: 23
<212> TYPE: DNA
<213> ORGANISM: Artificial sequence
<220> FEATURE:
<223> OTHER INFORMATION: Promoter

<400> SEQUENCE: 14
ggaaaatttt ttttcaaaag tac                                              23

<210> SEQ ID NO 15
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 15
ggaaaatttt ttttcaaaag tan                                              23

<210> SEQ ID NO 16
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 16
agaaattttt tttcgaaaaa can                                              23

<210> SEQ ID NO 17
<211> LENGTH: 23
<212> TYPE: DNA
<213> ORGANISM: Artificial Sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 17
taaaaatttt ttttgaaaag ggn                                              23

<210> SEQ ID NO 18
<211> LENGTH: 23
<212> TYPE: DNA
<213> ORGANISM: Artificial Sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 18
caaaaatatt tttgaaaaaa gan                                              23

<210> SEQ ID NO 19
```

```
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 19
ggaaatattt tttcataaac ccn                                              23

<210> SEQ ID NO 20
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 20
agaaaaatat tttcgaaaac tan                                              23

<210> SEQ ID NO 21
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 21
aaaaatattt tttcgaaaag tan                                              23

<210> SEQ ID NO 22
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 22
taaatttttt tttgcaaaag tan                                              23

<210> SEQ ID NO 23
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 23
acaaaaatat ttttcaaaac ccn                                              23
```

-continued

```
<210> SEQ ID NO 24
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 24
ttaaattttt tttcgtaaac ccn                                          23

<210> SEQ ID NO 25
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 25
ttaaattttt tttcataaac ccn                                          23

<210> SEQ ID NO 26
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 26
tcaaattttt ttttgcaaac ccn                                          23

<210> SEQ ID NO 27
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 27 caaattttttt tttgctaaac ccn                                         23

<210> SEQ ID NO 28
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 28
aaaaatattt ttttgaaaag tan                                          23
```

```
<210> SEQ ID NO 29
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 29
taaaaatatt tttcgtttac ccn                                              23

<210> SEQ ID NO 30
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 30
acaaaaatat ttttcgaaac ccn                                              23

<210> SEQ ID NO 31
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 31
tcaaattttt ttttgcaaag tan                                              23

<210> SEQ ID NO 32
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 32 tgaattttt tttcgtctac ccn                                               23

<210> SEQ ID NO 33
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 33
agaaaaatat ttttgaaaac tan                                              23
```

<210> SEQ ID NO 34
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 34
gcaaaataat tgtaaaaaag tan                                              23

<210> SEQ ID NO 35
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 35
agaaatttat tttaaaaaag ggn                                              23

<210> SEQ ID NO 36
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 36
tgaaaaatat ttttgaaaac tan                                              23

<210> SEQ ID NO 37
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 37
taaactattt tttcaaaaag gan                                              23

<210> SEQ ID NO 38
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 38

```
tgaaatattt tttgcgaaag ggn                                          23
```

<210> SEQ ID NO 39
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 39

```
taaacttttt ttttcgaaag tgn                                          23
```

<210> SEQ ID NO 40
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 40

```
tgaaatattt ttttgaaaac ccn                                          23
```

<210> SEQ ID NO 41
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 41

```
agatttttt tttgtaaaag tgn                                           23
```

<210> SEQ ID NO 42
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 42

```
gcaaaaatat ttcgtcaaac ccn                                          23
```

<210> SEQ ID NO 43
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 43

-continued

```
gaaaaatatt tttgataaag tan                                              23
```

<210> SEQ ID NO 44
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 44

```
gcaaaattat tttgctaaag tan                                              23
```

<210> SEQ ID NO 45
<211> LENGTH: 23
<212> TYPE: DNA
<213> ORGANISM: Artificial sequence
<220> FEATURE:
<223> OTHER INFORMATION: Promoter
<220> FEATURE:
<221> NAME/KEY: misc_feature
<222> LOCATION: (23)..(23)
<223> OTHER INFORMATION: n is any nucleotide

<400> SEQUENCE: 45

```
gaaaatatat ttttcaaaag tan                                              23
```

<210> SEQ ID NO 46
<211> LENGTH: 23
<212> TYPE: DNA
<213> ORGANISM: Artificial sequence
<220> FEATURE:
<223> OTHER INFORMATION: Promoter

<400> SEQUENCE: 46

```
ctcactcatt aggcaccccca ggc                                             23
```

<210> SEQ ID NO 47
<211> LENGTH: 20
<212> TYPE: RNA
<213> ORGANISM: Artificial sequence
<220> FEATURE:
<223> OTHER INFORMATION: Promoter

<400> SEQUENCE: 47

```
gcguuccugu acauaacccu                                                  20
```

<210> SEQ ID NO 48
<211> LENGTH: 20
<212> TYPE: RNA
<213> ORGANISM: Artificial sequence
<220> FEATURE:
<223> OTHER INFORMATION: Promoter

<400> SEQUENCE: 48

```
aguagugcaa agaaauuuaa                                                  20
```

<210> SEQ ID NO 49
<211> LENGTH: 20
<212> TYPE: RNA
<213> ORGANISM: Artificial sequence
<220> FEATURE:
<223> OTHER INFORMATION: Promoter

```
<400> SEQUENCE: 49
auguugucac gcuuuucguu                                              20

<210> SEQ ID NO 50
<211> LENGTH: 19
<212> TYPE: RNA
<213> ORGANISM: Artificial sequence
<220> FEATURE:
<223> OTHER INFORMATION: Promoter

<400> SEQUENCE: 50
aacgacagau ugugucgac                                               19

<210> SEQ ID NO 51
<211> LENGTH: 20
<212> TYPE: RNA
<213> ORGANISM: Artificial sequence
<220> FEATURE:
<223> OTHER INFORMATION: Promoter

<400> SEQUENCE: 51
uuccguuggg aucuuucgaa                                              20

<210> SEQ ID NO 52
<211> LENGTH: 20
<212> TYPE: RNA
<213> ORGANISM: Artificial Sequence
<220> FEATURE:
<223> OTHER INFORMATION: Promoter

<400> SEQUENCE: 52
gucagaguag ugucaagugu                                              20

<210> SEQ ID NO 53
<211> LENGTH: 20
<212> TYPE: RNA
<213> ORGANISM: Artificial sequence
<220> FEATURE:
<223> OTHER INFORMATION: Promoter

<400> SEQUENCE: 53
uaguacauaa ccuucgggca                                              20

<210> SEQ ID NO 54
<211> LENGTH: 20
<212> TYPE: RNA
<213> ORGANISM: Artificial sequence
<220> FEATURE:
<223> OTHER INFORMATION: Promoter

<400> SEQUENCE: 54
caucuaauuc aacaagaauu                                              20
```